(12) United States Patent
Becker et al.

(10) Patent No.: US 7,972,000 B2
(45) Date of Patent: Jul. 5, 2011

(54) METHOD AND ARRANGEMENT FOR DETERMINING THE INDIVIDUALLY REQUIRED ADDITION OF A VISION AID

(75) Inventors: B. Monique Becker, Aalen (DE); Jesús-Miguel Cabeza-Guillén, Aalen (DE); Timo Kratzer, Aalen (DE)

(73) Assignee: Carl Zeiss Vision GmbH, Aalen (DE)

( * ) Notice: Subject to any disclaimer, the term of this patent is extended or adjusted under 35 U.S.C. 154(b) by 0 days.

(21) Appl. No.: 12/656,143

(22) Filed: Jan. 19, 2010

(65) Prior Publication Data

US 2010/0182566 A1     Jul. 22, 2010

(30) Foreign Application Priority Data

Jan. 16, 2009   (DE) .................. 10 2009 004 866

(51) Int. Cl.
   *A61B 3/00* (2006.01)
(52) U.S. Cl. ........................ 351/246; 351/200
(58) Field of Classification Search .................. 351/200, 351/205, 246, 222
   See application file for complete search history.

(56) References Cited

U.S. PATENT DOCUMENTS

| | | | |
|---|---|---|---|
| 6,048,064 A | 4/2000 | Hosoi et al. | |
| 6,554,429 B1 | 4/2003 | Campin et al. | |
| 6,679,606 B2 | 1/2004 | Campin et al. | |
| 2004/0169820 A1 | 9/2004 | Dai et al. | |
| 2004/0169829 A1 | 9/2004 | Kwon | |
| 2008/0100800 A1 | 5/2008 | Guillen et al. | |
| 2008/0196086 A1 | 8/2008 | Schroeder et al. | |
| 2008/0231802 A2 | 9/2008 | Cabeza et al. | |

FOREIGN PATENT DOCUMENTS

| | | |
|---|---|---|
| DE | 10 2005 013 558 | 9/2006 |
| JP | 2001-21846 A | 1/2001 |
| JP | 2007-97707 A | 4/2007 |
| WO | WO 2008/047385 | 4/2008 |
| WO | WO 2008/047385 A1 | 4/2008 |
| WO | WO 2008/049503 A2 | 5/2008 |
| WO | WO 2008/064379 | 6/2008 |

OTHER PUBLICATIONS

B. Antona et al, "Comparing methods of determining addition in presbyopes", Clinical and Experimental Optometry, May 2008, pp. 313 to 318, 91:3, Optometrists Association Australia.

C. Leffler et al, "Clinical predictors of the optimal spectacle correction for comfort performing desktop tasks", Clinical and Experimental Optometry, Nov. 2008, pp. 530 to 537, 91:6, Optometrists Association Australia.

M. Millodot et al, "Presbyopia correction and the accommodation in reserve", Ophthal. Physiol. Opt., Apr. 1989, pp. 126 to 132, vol. 9, British College of Optometrists.

(Continued)

*Primary Examiner* — Jack Dinh

(74) *Attorney, Agent, or Firm* — Walter Ottesen

(57) ABSTRACT

The invention is directed to a method for determining the individually required addition (Add) of a vision assist for an eye, the method having the following steps:
   a) a preliminary addition ($Add_{preliminary}$) is determined;
   b) the depth of field (T) of the eye is individually determined; and,
   c) the addition (Add) is computed according to the following equation: $Add = Add_{preliminary} - \omega T$;
      wherein $\omega$ defines a real number which lies in the range $0 < \omega \leq 1$.

The invention is further directed to a corresponding arrangement for carrying out the method as well as a computer program.

43 Claims, 13 Drawing Sheets

OTHER PUBLICATIONS

D. Win-Hall et al, "Objective accommodation measurements in prepresbyopic eyes using an autorefractor and an aberrometer", J Cataract Refract Surg, 2008, pp. 774 to 784, 34, Elsevier, Inc.

J. Wold et al, "Subjective and objective measurement of human accommodative amplitude", J Cataract Refract Surg, 2003, pp. 1878 to 1888, 29, Elsevier, Inc.

DIN 5340-15, DIN 5340-12, DIN 5340-99, DIN 5340-20: Apr. 1998, pp. 2, 3, 8 and 9.

Born, Max et al, "Principles of Optics", Cambridge University Press, 7th (expanded) edition, pp. 370 to 373.

Diepes, Heinz, "Refraktionsbestimmung", Verlag Heinz Postenrieder, Pforzheim, 2nd edition, 1975, pp. 28, 29, 414 and 415.

Goersch, Helmut, "Wörterbuch der Optometrie", Verlag Bode Pforzheim, 2004, 2nd edition, pp. 2 and 3.

Goersch, Helmut, ed., "Handbuch für Augenoptik", Carl Zeiss, Oberkochen, 2000, pp. 3, 34 and 35.

Schwiegerling, Jim, "Scaling Zernike expansion coefficients to different pupil sizes", J. Opt. Soc. Am. A, vol. 19, No. 10, Oct. 2002, pp. 1937 to 1945.

Office Action Jul. 2010 (translation attached).

DIN 19 040 Apr. 1979 Part.5, pp. 1 to 7.

Translation of Japanese Office Action dated Jan. 25, 2011 for parallel Japanese application JP2010-007101.

Translation of Japanese Office Action dated Jan. 25, 2011 for parallel Japanese application JP2010-271744.

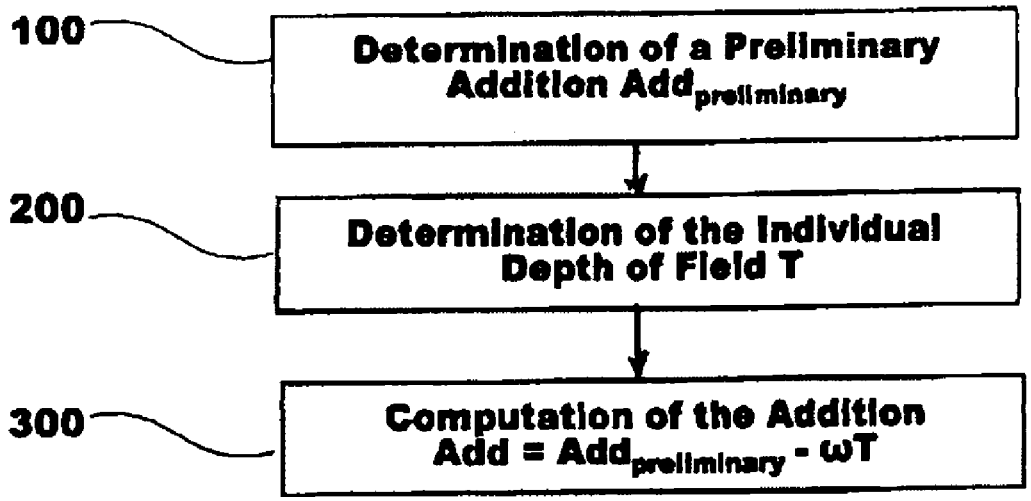
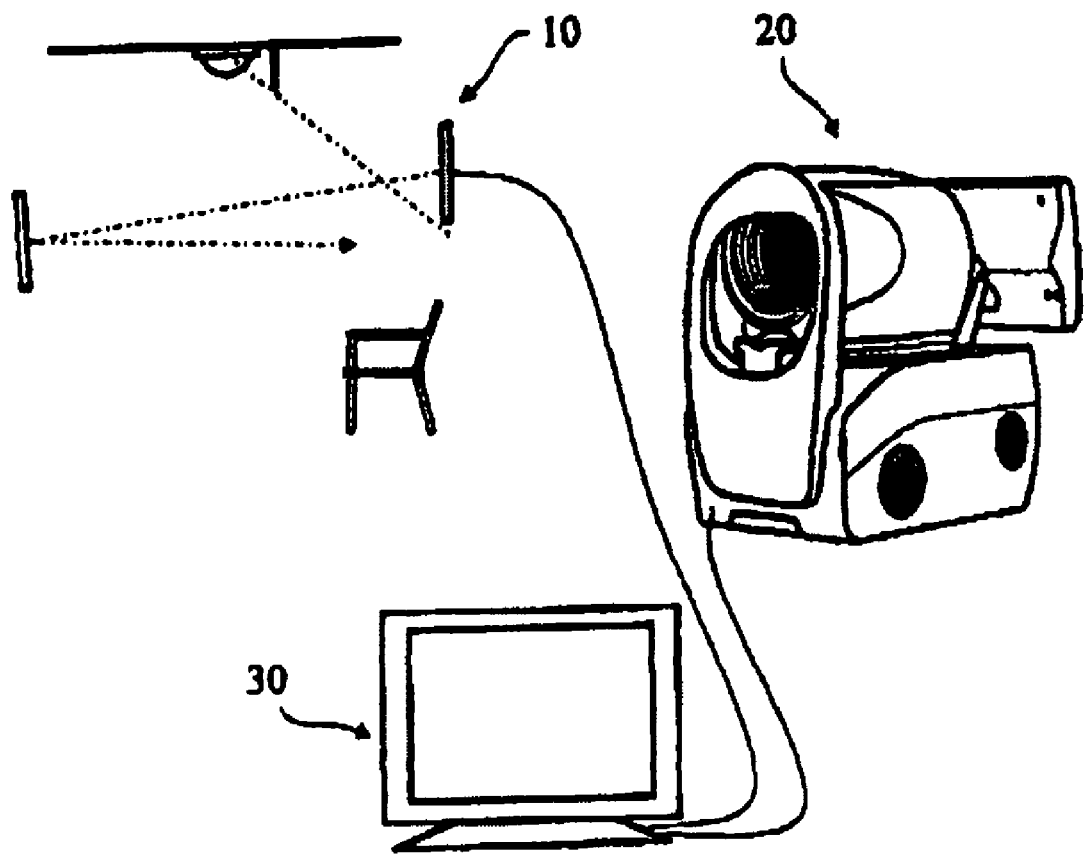

FIG.15 State of the Art

State of the Art ions during the adjustment of the eye on a near object (accommodation, convergence and synergistic pupil reflex) are characterized as accommodation triad or convergence reaction.

METHOD AND ARRANGEMENT FOR DETERMINING THE INDIVIDUALLY REQUIRED ADDITION OF A VISION AID

CROSS REFERENCE TO RELATED APPLICATION

This application claims priority of German patent application no. 10 2009 004 866.9, filed Jan. 16, 2009, the entire content of which is incorporated herein by reference.

FIELD OF THE INVENTION

The invention relates to a method for determining the individually required addition of a vision aid as well as a method for determining the individually required addition of a vision aid. The invention further relates to a computer adapted for carrying out the method and a computer program as well as a corresponding computer program product with a program code adapted for carrying out the method.

BACKGROUND OF THE INVENTION

In the following, a number of terms will be first defined to which reference will later be made.

The visual acuity or visus V is the extent of the capability of a living being to perceive patterns and contours as such in the outer world with the being's viewing organ. The dimensionless characteristic visus V is defined as $$V = 1'/(\text{individual angular visual acuity}) \quad (1)$$

wherein the angular visual acuity is the resolution power with which two viewing objects can still be perceived as separate (so-called minimum "separabile").

The depth of field or imaging depth T of the eye is, according to DIN 19040, 5-3.12, the magnitude of the region forward and rearward of the set point $A_E$ whereat the object points are imaged with a non-perceptible unsharpness of the retina image. The imaging depth T of the eye is dependent upon the pupil diameter and upon the central visual acuity. For a pupil diameter of 2.9 mm and a visual acuity V of 1.0, the imaging depth T results, theoretically, from the distances corresponding to 0.1 dpt on both sides of the set point $A_E$: 10 cm in the light direction behind the set point, 10 cm in light direction forward of the set point results in an imaging depth of 20 cm which corresponds to approximately 0.25 dpt (source: Helmut Goersch, Lexicon of Optometry, 2nd edition 2001).

Use distance $a_{use}$ is the distance, which is selected by a test person, from the eye principal point $H_A$ to the object.

The term addition Add or near addition is understood to mean the difference between the spherical effect of the near portion and that of the remote portion of a continuous vision lens or a multifocal spectacle lens.

Accommodation (from the Latin: accomodare "adapt, put on, fixing") characterizes operations for changing the light path within the eye in order to sharply image objects at different distances in the retina plane. In mammals and birds, the form of the elastic lens is changed in accordance with a theory of Helmholtz for accommodation in order to vary the refractive power. A theory of Schachar additionally proceeds from a forward displacement of the eye lens during the accommodation.

At the same time as the tensioning of the ciliary muscle, the eyes carry out a convergence movement, that is, the eyes move toward each other so that the viewing axes intersect at the fixation point. The convergence movement is, inter alia, a condition precedent for the fusion of the visual impressions of both eyes close in. Furthermore, a pupil constriction (convergence myosis) automatically occurs. The three coupled reactions during the adjustment of the eye on a near object (accommodation, convergence and synergistic pupil reflex) are characterized as accommodation triad or convergence reaction.

The far point refraction $A_R$ is the reciprocal of the far point distance $a_R$, that is, the distance $a_{object}$ of the location of the object from the object side principal point $H_A$ of the eye wherein the eye sharply perceives the object without accommodation. The adjusting point refraction $A_E$ is the reciprocal of the focusing point distance $a_E$ (also called: accommodation distance), that is, the distance $a_{object}$ of the object point, which, in the instantaneous accommodation state, is imaged in the fovea and is therefore sharply seen.

The accommodation-caused change of the focusing point refraction $A_E$ per unit of time is characterized as the accommodation speed $V_A$ in dpt/s. The accommodation speed $V_A$ results from the ratio of the change of the focusing point refraction $A_E$ to the accommodation time $t_A$. It is dependent upon the age and the focusing point refraction $A_{Ev}$, $A_{En}$ before and after the accommodation and amounts to approximately 2 to 5 dpt/s.

The accommodation requirement A, which is given in diopters (dpt) is understood, in accordance with DIN 5340-15, to be the reciprocal of the object distance $a_{object}$ (in meters) from the object side principal point $H_A$ of the eye. If an optical system is disposed forward of the eye, then the distance of the image developed by this system takes the place of the object distance $a_{object}$.

The relative accommodation $\Delta A_{rel}$ is defined in DIN 5340-12 as the change of the amplitude of accommodation $\Delta A$ for unchanged vergency position and unchanged sharp binocular normal vision. The change of the amplitude of accommodation $\Delta A$ is forcibly achieved by lenses having a spherical effect.

Mental accommodation $\Delta A_{psych}$ (proximal accommodation=instrument myopia) is understood to be the near accommodation $A_{near}$ triggered by real objects because of the consciousness of the nearness.

The accommodation stimulus $\Delta A_{stimulus}$ is the stimulus for accommodation which is triggered by a change of the fixation distance $a_{object}$ by the retina image which is at first unsharp.

The amplitude of accommodation $\Delta A$, which is likewise given in diopters (dpt), is understood according to DIN 5340-99 to be the difference between the far point refraction $A_R$ and the set point refraction $A_E$. The term amplitude of accommodation $\Delta A$ is also known as external accommodation.

The DIN 5340-20 defines the maximum amplitude of accommodation or the maximum amplitude of accommodation $\Delta A_{max}$ as the difference between the far point refraction $A_R$ and the near point refraction $A_p$. The near point refraction $A_p$ is the reciprocal of the distance $a_p$ of the eye principal point $H_A$ to the sharply viewed object point with strongest accommodation.

For infants, the maximum amplitude of accommodation $\Delta A_{max}$ is approximately 14 dpt. Referred to the total refractive power of the eye of approximately 58 dpt, this corresponds to a variation of approximately 25%. At an old age, the maximum amplitude of accommodation $\Delta A_{max}$ drops to values under 2 dpt or 4%. For this reason, the smallest distance, that is, the near point $a_p$, wherein objects can still be sharply seen is magnified from approximately $a_p$=7 cm for infants to more than $a_p$=50 cm in persons of old age.

An exact separation between maximum amplitude of accommodation $\Delta A_{max}$ and depth of field T of the human eye is to date not possible. The sum from actual maximum amplitude of accommodation $\Delta A_{max}$, which is defined by the above-mentioned mechanisms of the accommodation triad and the depth of field T is therefore referred to hereinafter as physiological maximum amplitude of accommodation $\Delta A^*_{max}$.

In 1922, Duane determined the age dependency of the average physiological maximum amplitude of accommodation $\Delta A^*_{max,m}$ from the viewing impressions of 5,000 test persons having normal vision. In the determination of this data, no distinction was drawn between the maximum amplitude of accommodation $\Delta A_{max}$ and the depth of field T, that is, the determined curve is a superposition of both effects. The middle curve 802 of the diagram of FIG. 15 shows this age dependency of the average physiological maximum amplitude of accommodation $\Delta A^*_{max,m}$. The upper and the lower curves (804, 806) represent the respective physiological limits of the dispersion. The diagram of FIG. 16 shows the corresponding age dependency of the minimum visual distance $a_p$.

The reason for the reduction of the maximum amplitude of accommodation $\Delta A_{max}$ is a decreased elasticity of the lens capsule or a lens thickening because of lifelong growth of the lens shell (Helmholtz theory). The elasticity decreases with increasing age. It was determined that even for vanishing elasticity of the lens capsule, a residual of accommodation amplitude $\Delta A_{max}$ remains. The so-called Schachar theory according to which, additionally, one proceeds from a forward displacement of the eye lens during the accommodation can explain the remaining residual of maximum amplitude of accommodation $\Delta A_{max}$ which is not lost with increasing age.

If the maximum amplitude of accommodation $\Delta A_{max}$ including the depth of field T drops, with increasing age (see FIG. 15) below approximately 3 diopters (the newspaper must be held at a distance of over 35 cm for reading with distance spectacles), one speaks of presbyopia. Simple reading spectacles, bifocal spectacles, continuous vision spectacles or multifocal contact lenses or intraocular lenses can compensate for the presbyopia.

The term use accommodation $\Delta A_{use}$ is understood to be that accommodation A which can be provided without difficulty over a longer time span. It amounts to approximately ½ (Reiner) to ⅔ (Schober) of the maximum amplitude of accommodation $\Delta A_{max}$.

From the state of the art, a great number of methods are known for determining an addition $A_{dd}$ of multifocal or continuous vision spectacle lens, contact lens or intraocular lens with this addition Add being suitable for an ametropic person and being adapted to that person's requirements. All these methods have in common that the addition Add should not exceed the reciprocal value of the minimum use distance $a_{use,min}$. The methods, however, differ from each other in the determination of the actual value of the addition Add. This subject matter is explained in the following based on a simple computation example.

It is assumed that a test person experiences as pleasant to hold a document at a distance of 40 cm to the eye when reading. This distance is identified hereinafter as the use distance $a_{use}$. Furthermore, it is assumed that the minimum use distance $a_{use,min}$ at which the test person holds the reading material is 33 cm at any time. The reciprocal of the minimum use distance $a_{use,min}$ amounts to 3 dpt. These 3 dpt define the accommodation requirement A for the minimum use distance $a_{use,min}$.

If the test person were, for example, 50 years old, then the test person would have a residual maximum amplitude of accommodation $\Delta A_{max}$ of approximately 2 dpt according to the diagram of Duane of FIG. 15. Because the actually used accommodation effort, that is, the use accommodation $\Delta A_{use}$ according to the theory of Reiner is approximately half (according to the theory of Schober approximately two thirds) of the still remaining accommodation amplitude $\Delta A_{max}$, the test person would actually use approximately 1 dpt (up to 1.5 dpt according to Schober) of his or her maximum amplitude of accommodation $\Delta A_{max}$. The correct addition Add for a spectacle lens, contact lens or intraocular lens for the test person for the above-given minimal use distance $a_{use,min}$ of the test person of approximately 33 cm would therefore amount to 2 dpt according to Reiner (or 1.5 dpt according to Schober).

In this example, the document is disposed during reading mostly at a use distance $a_{use}$, that is, the reading distance of 40 cm to the eye of the test person (the reciprocal $1/a_{use}$ of this is 2.5 dpt). For this reason, for a use accommodation $\Delta A_{use}$ of approximately 1 dpt (or 1.5 dpt according to Schober), an addition Add of 1.5 dpt (or 1 dpt according to Schober) would, in a satisfactory manner, satisfy the requirements of the test person. Because of the test person's residual maximum amplitude of accommodation $\Delta A_{max}$ (including depth of field T), the test person is able, at a reading distance $a_{use}$ of 33 cm, with an addition Add of only 1.5 dpt (or 1 dpt according to Schober) to see sharply. The addition Add of the spectacle lens, contact lens or intraocular lens therefore amounts to 1.5 dpt according to the theory of Reiner (or 1.5 dpt according to Schober) and should not exceed 2.0 dpt. The addition Add is optimally adapted to the requirements of the test person.

Unfortunately, in present day practice, mostly higher additions Add are prescribed which often leads to dissatisfaction of the wearer of the vision aid having the resulting lens design.

The following sections present an overview as to the most often used methods according to the applicants for determining the addition Add of a spectacle lens, contact lens or intraocular lens and the inadequacies of the method in each case.

Method 1. Addition Determination Based on an Estimation Table

The most often used method for determining the addition is made with an estimation table presented below as Table 1.

TABLE 1

| Estimation Table for Determining the Addition of a Spectacle Lens, Contact Lens or Intraocular Lens | | |
|---|---|---|
| Age (Years) | Addition Add (dpt) for a Use Distance of 33 cm | Addition Add (dpt) for a Use Distance of 40 cm |
| 45 | 1.0 | 0.75 |
| 45 . . . 48 | 1.5 | 1.00 |
| 48 . . . 50 | 2.0 | 1.25 |
| 50 . . . 65 | 2.5 | 1.75 |

This estimation table is oriented to the average physiological accommodation amplitude $\Delta A^*_{max,m}$ of the age category and the desired use distance $a_{use}$. The estimation table is based on the curve of Duane shown in FIG. 15 and described above.

In this method, the use distance $a_{use}$, which is suitable for the test person, is first determined. This distance, which is used the most by the test person, is between the object end principal point $H_A$ of the eye and the object to be perceived. The addition Add is then estimated in correspondence to the age of the test person based on the above-shown table.

This method is based exclusively on estimates and considers only the age and the use distance $a_{use}$. For this reason, it is very inaccurate. The inadequacies of this method were known earlier. Methods were developed which made a check possible and, if needed, also made possible a correction of the addition Add determined on the basis of the estimation table. Some selected examples are presented hereinafter.

Method 2. Determination of Addition Based on the Estimation Table of Method 1 with Red-Green Contrast Compensation In this method, red and green optotypes are presented binocularly to the test person at the corresponding use distance $a_{use}$. These optotypes have the dioptric effect corresponding to the addition $Add_{preliminary}$ determined with the method described under method 1. The test person compares the optotypes as to contrast equality. Specifically, the test person compares the brightness of the red and green foci of the optotypes. If the red focus of the optotype appears to be darker, the addition Add must be reduced or the object distance $a_{use}$ must be increased. If the green focus of the optotypes appears darker, then the addition Add must be increased or the object distance $a_{use}$ must be reduced. If the brightness of the optotypes having red and green foci are found to be equal, then the corresponding addition Add is correct.

This method too is very imprecise because it likewise is based on the use of the above-mentioned estimation table. Furthermore, the method is based on the subjective perception of the test person. If the test person indicates spontaneously that all optotypes are seen with the same brightness, the optician then must change the object distance $a_{use}$ in order to check whether the test person even reacts to the test. Furthermore, it has been shown that test persons under 50 years of age do not accommodate precisely to the object plane; rather, they accommodate slightly ahead of this plane. This difference is compensated by the depth of field T of the human eye with the effect that the optician determines too high an addition Add. Depending upon age, a corrective amount is subtracted corresponding to the Table 2 set forth below.

Table 2: Corrective Amount for Addition Add of a Spectacle Lens, Contact Lens or Intraocular Lens Determined in Accordance with a Red-Green Contrast Compensation

| Age (Years) | Corrective Amount (dpt) |
| --- | --- |
| under 50 | 0.5 |
| 50 ... 60 | 0.25 |

This method is very inaccurate because it is based only on estimates and only the age, use distance $a_{use}$ and the binocular contrast are considered.

Method 3. Determination of Addition While Considering the Subjectively Determined Accommodation Amplitude In this method, a suitable vision test (for example, the so-called line figure of Duane) is presented to the test person at an adequately long distance. Thereafter, the distance between eye and test character is continuously reduced until the test person indicates that he or she perceives the test character as unsharp. The reciprocal of this distance between object and principal point $H_A$ corresponds to the maximum amplitude of accommodation $\Delta A_{max}$ inclusive of the depth of field T of the eye. As addition Add, one takes half of this reciprocal value in accordance with the suggestion of Reiner. Reiner assumes that the actual use accommodation $\Delta A_{use}$ amounts to just half the maximum amplitude of accommodation $\Delta A^*_{max}$. Schober suggests a factor of ⅔ in lieu of a factor of ½.

If the test is carried out monocularly, then the accommodation stimulus (accommodation stimulus $\Delta A_{stimulus}$) is triggered exclusively by the retinal unsharpness and the consciousness of the closeness; whereas, in the binocular test, the convergence of the eyes also influences the accommodation stimulus $\Delta A_{stimulus}$. Binocular viewing increases the maximum amplitude of accommodation $\Delta A_{max}$ by approximately 0.5 dpt.

The method considers only the subjectively determined physiological accommodation amplitude $\Delta A^*_{max}$ which is computed from the sum of the actual accommodation amplitude $\Delta A_{max}$ and the depth of field T:

$$\Delta A^*_{max} = \Delta A_{max} + T \qquad (2)$$

and the estimated use accommodation $\Delta A_{use}$ and is therefore very imprecise.

Method 4. Determination of Addition While Considering the Relative Accommodation In this method, a suitable addition $Add_{preliminary}$ is first determined, again, with the estimation table (Table 1) while applying the method described under method 1. Thereafter, a suitable vision sample (for example, Duane's line figure) is fixated at the use distance $a_{use}$. The addition $Add_{preliminary}$ is now increased to the addition Add+ whereat the test person just still sees sharply. Thereafter, the addition $Add_{preliminary}$ is reduced up to the addition Add− whereat the test person still just sees sharply. The sum of the strongest addition Add+ and the weakest addition Add− divided by two yields the necessary addition $$Add = (Add+ + Add-)/2 \qquad (3)$$

The method considers exclusively the age, use distance $a_{use}$, the relative accommodation $\Delta A_{rel}$ and an estimate of the use accommodation $\Delta A_{use}$ and is therefore imprecise.

All of the above-described methods for determining the addition Add according to the known state of the art described therefore exhibit inaccuracies because they are based on assumptions or estimates. Since all of the methods are subjective methods, they continue to be burdened generally with the disadvantages of subjective measuring methods (namely, inter alia, validity of the statements of the test person, perception of the test person in the measuring situation, et cetera).

SUMMARY OF THE INVENTION

In view of the above, it is an object of the invention to provide a method of determining the individually needed addition of a vision aid which is more precise compared to the state of the art and it is another object of the invention to provide an arrangement suitable for carrying out the method of the invention.

The inventors have established that most of the above-described methods are based on the age and the standard use distance $a_{use}$ of 40 cm and the actual maximum amplitude of accommodation $\Delta A_{max}$, the actual depth of field T as well as the habits of the test person were not or only inadequately considered. This fact has the consequence that the addition Add, in general, is assumed too high. An unnecessarily high addition Add deteriorates the design in form of reductions of the usable vision regions, primarily, in the intermediate region and near region of the corrective lens with noticeable disadvantages arising therefrom for the wearer of the spectacles.

The invention is based on the idea to consider the depth of field T of the eye and/or to individually determine characteristics of the eye of the particular test person, which up to now have only been estimated, and based on these preferably objectively determined characteristics, to determine the required and best suitable addition Add of the vision aid for the test person.

A method of the invention for determining the individually required addition Add of a vision aid for the eye includes the following method steps:
a) determination of a preliminary addition $Add_{preliminary}$, for example, with one of the methods described above;
b) determination of the individual depth of field T of the eye; and,
c) computation of the addition Add in accordance with the following equation:

$$Add = Add_{preliminary} - \omega T \quad (4)$$

wherein $\omega$ is a real number which lies in the range of $0 < \omega \leq 1$. Usually, the values for $\omega$ lie in the range of $1/4 \leq \omega \leq 3/4$. Suitable values for the factor $\omega$ for weighting the depth of field T are therefore, for example, 0.5 or $2/3$.

The corresponding arrangement for carrying out the method accordingly includes the following components:
a) an addition determination unit for determining a preliminary addition $Add_{preliminary}$ for an eye of a test person;
b) a depth of field determination unit for determining the individual depth of field T of the eye of the test person; and,
c) a computation unit for computing the addition Add in accordance with the above equation (4).

A further method according to the invention for determining the individually required addition Add of a vision aid for the eye includes the following method steps:
a) the maximum amplitude of accommodation $\Delta A_{max}$ is individually and objectively determined;
b) the use distance $a_{use}$ is individually determined; and,
c) the addition Add is computed in accordance with the following equation:

$$Add = 1/a_{use} - \sigma \Delta A\ max \quad (5)$$

wherein $\sigma$ is a real number which lies in the range of $0 < \sigma < 1$. Mostly, the values for $\sigma$ lie in the interval $1/4 \leq \sigma \leq 3/4$. $\sigma$ can therefore, for example, be $1/2$, $2/3$ or $5/12$.

A corresponding arrangement according to the invention includes:
a) a maximum amplitude of accommodation determination unit for individually and objectively determining the maximum amplitude of accommodation $\Delta A_{max}$;
b) a use distance determination unit for individually determining the use distance $a_{use}$; and,
c) an addition computation unit for computing the addition Add according to equation (5).

The methods according to the invention set forth above can, for example, be performed on a computer which is correspondingly adapted to carry out the particular method.

A computer program or a computer program product having a computer code for carrying out the particular method can be provided on a computer. The computer program can be stored on a machine readable data carrier.

The preliminary addition $Add_{preliminary}$ can, for example, be determined based on an estimate of the physiological accommodation amplitude $\Delta A^*_{max}$. For example, the above-described diagram of Duane can be used. The computation of the preliminary addition $Add_{preliminary}$ can, for example, take place with the aid of method 1 or method 2 described above. These methods for computing the preliminary addition $Add_{preliminary}$ are characterized in that they are known by the opticians applying the same. An education of the opticians for applying the method of the invention is therefore, for the most part, not needed.

The preliminary addition $Add_{preliminary}$ can also be determined based on an estimate of the actual maximum amplitude of accommodation $\Delta A_{max}$. An estimate of the actual maximum amplitude of accommodation $\Delta A_{max}$ can, for example, come about in that the test person brings a suitable reading sample so close to the eye until the reading sample just appears unsharp. The reciprocal of the distance $a_{use}$ of the reading sample, which is measured in meters, to the principal point $H_A$ of the eye of the test person yields the maximum amplitude of accommodation $\Delta A_{max}$.

An estimate of the use accommodation $\Delta A_{use}$ can likewise serve as the basis of the determination of the preliminary accommodation $Add_{preliminary}$. The use accommodation $\Delta A_{use}$ is, for example, assumed to be half of the maximum amplitude of accommodation $\Delta A_{max}$ according to Reiner. Schober assumes this to be $2/3$ of the maximum amplitude of accommodation $\Delta A_{max}$.

The preliminary addition $Add_{preliminary}$ can, for example, also be computed based on an individual measurement of the physiological maximum amplitude of accommodation $\Delta A^*_{max}$. The example, which is described in the introduction as method 3 sets forth a suggestion for determining the preliminary addition $Add_{preliminary}$ according to this method.

The determination of the physiological maximum amplitude of accommodation $\Delta A^*_{max}$ can, for example, also take place in that the near point is monocularly determined at the distance $a_p$ by applying a suitable test figure by the test person who is fully corrected for the distance. As known, the near point requires the highest stretching of the accommodation. For this reason, it is necessary to carry out the measurement as rapidly as possible, namely, within the accommodation time $(t < t_A)$. Otherwise, one encounters the problem of not measuring the physiological maximum amplitude of accommodation $\Delta A^*_{max}$ but the use accommodation $\Delta A_{use}$. The physiological maximum amplitude of accommodation $\Delta A^*_{max}$ then results from the reciprocal of the near point distance $a_p$ measured in meters:

$$\Delta A^*_{max} = 1/a_p \quad (6)$$

Another possibility is to position a suitable test figure at a set distance $a_E$ of, for example, 40 cm (corresponds to a focusing point refraction $A_E$ of 2.5 dpt) to the eye principal point $H_A$ of the test person. If the test person sees the test figure sharply, negative spherical lenses are added binocularly until the test figure is just blurred. If the test person does not see the test figure sharply, then positive spherical lenses are added binocularly until the test figure appears just so to be sharp. The value $S'_{binocular}$ of the spherical effect of the lens which is determined with negative or positive spherical lenses is noted. The physiological maximum amplitude of accommodation $\Delta A^*_{max}$ then results from the equation:

$$\Delta A^*_{max} = A_E - S'_{binocular} \quad (7)$$

wherein: $A_E = 2.5$ dpt. A disadvantage of this possibility is defined by the convergence caused by the binocular measuring situation.

A further possibility of determining the physiological maximum amplitude of accommodation $\Delta A^*_{max}$ is described hereinafter.

Based on the curve of FIG. 16, a suitable test figure is presented to the test person at a corresponding distance $a_{use}$ (the distance $a_{use}$ corresponds to the minimum visual distance $a_p$ which is average for the age of the test person). If the test figure is recognized as being sharp there, negative spherical lenses are added monocularly until the test figure is just blurred. If the test figure is not recognized as being sharp, positive spherical lenses are added monocularly until the test figure is just blurred. The individual physiological maximum amplitude of accommodation $\Delta A^*_{max}$ then results from the reciprocal of the average minimal distance $a_{pDuane}$, (corresponds to the mean physiological maximum amplitude of accommodation $\Delta A^*_{max}$ from the mean curve 802 of the diagram of FIG. 15) and the determined value for the pregiven lenses $S'_{monocular}$. For this, the following equation applies:

$$\Delta A^*_{max} = \Delta A^*_{max,m} - S'_{monocular} \quad (8)$$

wherein $$\Delta A^*_{max,m} = 1/a_{pDuane} \quad (9)$$

In the three methods described in detail above, an accommodation meter can be used as shown in FIG. 17 (from Heinz Diepes, "Refraction Determination", Publisher Heinz Postenrieder, Pforzheim, 2nd edition, 1975, page 414).

An individual measurement of the actual maximum amplitude of accommodation $\Delta A^*_{max}$ can also be carried out. In the meantime, for example, it is known from U.S. Pat. No. 6,554,429 B1 to objectively determine the actual maximum amplitude of accommodation $\Delta A_{max}$ with the aid of a wavefront measurement. Carrying out the method while considering the objectively determined maximum amplitude of accommodation $\Delta A_{max}$ improves the accuracy significantly.

Finally, a measurement of the actual individual use accommodation $\Delta A_{use}$ can be carried out and based on this, the preliminary addition $Add_{preliminary}$ can be determined. An example is defined in the introductory description under the method described in method 4.

For the determination of the use accommodation $\Delta A_{use}$, an estimated addition $Add_{estimated}$ can also be placed in the measurement spectacle for the test person who is fully corrected for distance. The test person is then requested to bring a suitable test figure monocularly so close to the eye until the test person recognizes the test figure as just being still sharp. This corresponds to the near point distance $a_p$. The test person is then requested to view the test figure monocularly until it appears unsharp because of the diminishing accommodation $\Delta A$. In a next step, the test person should hold the test figure so far away from himself or herself until it again appears sharp (corresponds to set point $a_E$). The reciprocal of the distance $a_E$ (measured in meters) to the set point yields the use accommodation $\Delta A_{use}$:

$$\Delta A_{use} = 1/a_E \quad (10)$$

In a special configuration of the invention, a use distance $a_{use}$ can also be determined and the preliminary addition $Add_{preliminary}$ can be computed according to the following equation:

$$Add_{preliminary} = 1/a_{use} - \sigma \Delta A_{max}, \quad (11)$$

wherein $\sigma$ is a real number which lies in the range $0 \leq \sigma \leq 1$. Since the preliminary addition $Add_{preliminary}$ is a pure computation quantity, it can actually also be set equal to the reciprocal of the use distance $a_{use}$.

The use distance $a_{use}$ can, for example, be individually determined in that a test person is offered an object and, as the use distance $a_{use}$, the distance from the object end principal point $H_A$ of the eye to the location is assumed whereat the object is found by the test person during relaxed viewing. The individual determination of a use distance $a_{use}$ of the test person is not necessarily limited to the desired reading distance and can, instead, be determined for all other desired distances such as work on a computer having a monitor.

The use distance $a_{use}$ can also be determined by the test person from the medical history with indications of the primary viewing tasks and the distances corresponding thereto. Both of the above methods define subjective methods which can be objectified up to a certain degree with suitable questions to the test person.

It is often, however, more precise to objectively individually determine the use distance $a_{use}$. Objectively, the use distance $a_{use}$ can, for example, be determined in that a measuring device automatically measures one or more use distances important for the test person and averages these as needed. WO 2008/054379 A1 describes, for example, an arrangement for detecting the reading vision sharpness with which also the use distance $a_{use}$ can De determined. Means are provided which measure the reading distance $a_{use}$, which is freely selectable by the test person, from the illustrated text or the illustrated graphic on a presentation surface.

The maximum amplitude of accommodation $\Delta A_{max}$ can be determined individually and objectively with the aid of different apparatus. The actual maximum amplitude of accommodation $\Delta A_{max}$ can, as already indicated above, be determined from a wavefront measurement. Accordingly, for determining the maximum amplitude of accommodation $\Delta A_{max}$, a wavefront measuring unit can be used such as a wavefront sensor as, for example, a Shack-Hartmann sensor. A method for determining the maximum amplitude of accommodation $\Delta A_{max}$ with the aid of a wavefront sensor is, as already was indicated above, shown in, for example, U.S. Pat. No. 6,554,429 B1 (see especially column 3, line 23, to column 4, line 25 and claim 1). There, different types of suitable sensors are also indicated (see there column 3, lines 10 to 13).

The actual maximum amplitude of accommodation $\Delta A_{max}$ can, however, alternatively also be determined as a difference between the far point refraction $A_R$, which is determined objectively from a wavefront measurement or an autorefraction measurement of the eye, and the near point refraction $A_p$ which is objectively determined from a wavefront measurement or an autorefraction measurement of the eye.

Specifically, this determination of the actual maximum amplitude of accommodation $\Delta A_{max}$ takes place, for example, with the following steps:

a) A wavefront of a light beam having a predetermined wavefront, which is reflected at the retina and impinges on the non-accommodating eye, is measured or an autorefraction of the non-accommodating eye is measured. Preferably, no accommodation stimulus $\Delta A_{stimulus}$ is presented to the eye.

b) From the wavefront measured in step a) or the autoreflection measured in step a), a far point refraction $A_R$ of the eye is computed.

c) Thereafter, an accommodation stimulus $\Delta A_{stimulus}$, which exceeds the actual maximum amplitude of accommodation $\Delta A_{max}$, is presented for the eye.

d) Then, a wavefront of a light beam with a predetermined wavefront, which is reflected at the retina and impinges on the eye accommodating because of the accommodation stimulus $\Delta A_{stimulus}$, is measured or an autorefraction of the eye, which is accommodating because of the accommodating stimulus $\Delta A_{stimulus}$, is measured. Specifically, this takes place in that the fixation distance $a_E$ (that is, the distance from the eye principal point $H_A$ to the focusing point of the eye) is so selected that the eye is no longer able to sharply perceive the object located in the fixation point.

e) From the wavefront measured in step d) or the autorefraction measured in step d), the actual focusing point refraction $A_E$ of the eye is computed, f) The actual focusing point refraction $A_E$, which is computed in step e), is compared to the focusing point refraction $A_{E,ideal}$, which is identified hereinafter as ideal, which would result if the accommodation A of the eye could follow the accommodation stimulus $\Delta A_{stimulus}$.

g) Thereafter, the accommodation stimulus $\Delta A_{stimulus}$ is continuously reduced or reduced in discrete steps, for example, 0.05 dpt, and the actual focusing point refraction $A_E$ is continuously measured corresponding to steps e) and f) and is compared to the ideal focusing point refraction $A_E$.

h) As a near point refraction $A_p$, for example, the actual focusing point refraction $A_E$ is then selected which, with the comparison carried out under step g), follows, for the first time, the change of the ideal focusing point refraction $A_E$.

Alternatively, it is possible after step e) to reduce the accommodation stimulus $\Delta A_{stimulus}$ continuously or in discrete steps and to continuously measure the actual focusing point refraction $A_E$ corresponding to steps e) and f) and to use as near point refraction $A_p$ the measured actual focusing point refraction $A_E$ (or one of the measured actual focusing point refractions or a mean value of the measured actual focusing point refractions) for which the measured focusing point refraction $A_E$ no longer follows the accommodation stimulus $\Delta A_{stimulus}$.

As a further alternative, it is possible, in lieu of method of step c), to present to the eye an accommodation stimulus $\Delta A_{stimulus}$, which the eye can follow without difficulty, and then to increase the accommodation stimulus $\Delta A_{stimulus}$ continuously or in discrete steps until (and, if needed, somewhat thereabove) the accommodation A of the eye can no longer follow this stimulus $\Delta A_{stimulus}$. The method steps d) to h) can then; for example, be processed in a corresponding manner. As a near point refraction $A_p$, for example, the actual focusing point refraction $A_E$ is then selected which, with the comparison carried out under step g) ideally follows for the last time the change of the ideal focusing point refraction $A_E$. It is understood that also as a near point refraction $A_p$, the measured actual focusing point refraction $A_E$ (or one of the measured actual focusing point refractions or a mean value of the measured actual focusing point refraction $A_E$) can be used wherein the measured focusing point refraction $A_E$ just no longer follows the accommodation stimulus $\Delta A_{stimulus}$.

The preliminary addition $Add_{preliminary}$ can, for example, be computed after completed determination of the use distance $a_{use}$ according to the following equation:

$$Add_{preliminary} = 1/a_{use} - \Delta A_{use}. \tag{12}$$

The actual use accommodation $\Delta A_{use}$ can, for example, be measured as follows.

The same measurement as already described with respect to the measurement of the maximum amplitude of accommodation is carried out only with the difference that the measurement takes longer and the particular accommodation stimulus $\Delta A_{stimulus}$ is presented to the eye for several seconds and ideally so long until the accommodation A completely follows the stimulus $\Delta A_{stimulus}$. The duration t of the accommodation stimulus $\Delta A_{stimulus}$ is therefore selected greater than the accommodation time $t_A$.

For the determination of the use accommodation $\Delta A_{use}$, the test person, who is completely corrected for distance, is asked to monocularly bring a suitable test figure so close to the eye until he or she can just recognize the same as sharp. This test figure can, for example, be shown on an accommodometer as shown in FIG. 17. The distance so determined corresponds to the near point distance $a_p$. If the length of the accommodometer rail (or, if the measurement is undertaken without an accommodometer, the arm length of the test person) is insufficient because of a high degree of presbiopy, then the investigator, based on suspicion, adds a spherical near addition which later is subtracted from the measured use accommodation $\Delta A_{use}$. The test person is now requested to view monocularly the test figure so long until the test figure appears unsharp because of reducing accommodation $\Delta A$. In the next step, the test person is asked to hold the test figure so far away until it again appears to be sharp (corresponds to the focusing point $a_E$). The reciprocal of the distance measured in meters to the focusing point $a_E$ yields the use accommodation $\Delta A_{use}$.

The preliminary addition $Add_{preliminary}$ can, for example, be computed according to conventional methods from the far point refraction $A_R$ and the near point refraction $A_p$ in accordance with the following equation:

$$Add_{preliminary} = A_p - A_R \tag{13}$$

The depth of field T corresponds just to twice the maximum accommodation stimulus $\Delta A_{stimulus}$ whereat the eye just not yet accommodates.

The use of a wavefront measuring device for determining the depth of field T is absolutely required here. The use of an autorefraction measuring unit by itself is not possible for determining the depth of field T. For aphakia or pseudophakia, only the last mentioned method is possible for the determination of the depth of field T on the basis of a measurement with a wavefront measuring unit.

The individual depth of field T of the test person can be determined, for example, from a sequence of wavefront measurements or a sequence of autorefraction measurements for fixation distances in the closer vicinity of the far point. As a maximum accommodation stimulus $\Delta A_{stimulus}$, one takes, for example, the accommodation stimulus $\Delta A_{stimulus}$ (corresponding to the reciprocal of the fixation distance) for which the measured focusing point refraction $A_E$ just departs from the far point refraction $A_R$ determined from a wavefront measurement or an autorefraction measurement or just still corresponds to the corresponding far point refraction $A_R$. As maximum accommodation stimulus $\Delta A_{stimulus}$, one can also take the accommodation stimulus $\Delta A_{stimulus}$ wherein the measured wavefront just still coincides with the wavefront for infinite fixation distance or wherein the measured wavefront just slightly deviates from the wavefront at infinite fixation distance.

A further method for determining the depth of field T on the basis of a wavefront analysis can, for example, include the following method steps:

a) A wavefront, which is reflected at the retina, of a beam with a predetermined wavefront impinging on the non-accommodating eye or an autorefraction of the non-accommodating eye is measured. Preferably, the eye is presented with no accommodation stimulus.

b) In advance, at the same time or thereafter, the pupil diameter of the eye is measured. What is essential here is that the pupil diameter is measured in the state after step a). The measurement of the pupil diameter can, for example, take place in that a camera recording is made of the eye and the diameter of the pupil is taken from the recording.

c) Thereafter, the conversion of the measured wavefront to a desired pupil diameter takes place. In the article by J. Schwiegerling entitled "Scaling Zernike expansion coefficients to different pupil sizes", published in the J. Opt. Soc. Am. A, Vol. 19, No. 10 on pages 1937 to 1945, possibilities for conversion are shown.
d) In a further step, a fixation target is made available with an illustration of structures having pregiven spatial frequencies corresponding to the desired requirements, for example, Visus V=0.4 when reading.
e) Thereafter, the fixation of an examining range of, for example, +/−5 dpt or +/−3 dpt about an average sphere mSph=the far point refraction $A_R$ takes place, for example, in steps of 0.05 dpt or 0.1 dot wherein:

$$mSph = Sph + \frac{Zyl}{2} \quad (14)$$

wherein Sph is the spherical effect and Zyl is the astigmatic effect of a vision aid provided for the test person.
f) Thereafter, a convolution of the wavefront takes place about the mean sphere $mSph_{corr}$ which is pregiven by the particular point in the search space. This corrected wavefront is then convoluted with the structures of the fixation target. This convolution serves to simulate the visual impression of the test person with a wavefront changed in the search space.
g) The subsequent evaluation of the convolution comprises, for example, the determination of the ratio Q from the maximum and minimum intensities ($I_{max}$, $I_{min}$) of the structures arising because of the folding:

$$Q = \frac{I_{max} - I_{min}}{I_{max}} \quad (15)$$

h) The steps f) and g) are now carried out for all values $mSph_{corr}$ within the search space. In this way, one obtains a value for the ratio Q for each $mSph_{corr}$.

For the depth of field T, the amount of the difference of the values of the mean sphere $mSph_{corr}$ in the search space are taken wherein the ratio Q just exceeds or is just less than a pregiven ratio $Q_{pre}$. In "Principles of Optics", Cambridge University Press, 7th expanded edition, pages 370 to 371, Max Born et al provide, for example, as threshold, whereat mutually adjacent structures are just perceivable as being separate, a ratio Q of the intensity difference $I_{max}-I_{min}$ for the maximum intensity $I_{max}$ of 19% (so-called Rayleigh criterion):

$$Q = \frac{I_{max} - I_{min}}{I_{max}} = 0.19 \quad (16)$$

Another method for determining the depth or field T on the basis of wavefront analysis can include the following method steps:
a) A wavefront, which is reflected at the retina, of a light beam with a predetermined wavefront, which impinges on the non-accommodating eye, is measured or an autorefraction of the non-accommodating eye. Preferably no accommodation stimulus $\Delta A_{stimulus}$ is presented to the eye.
b) In advance, simultaneously or thereafter, the pupil diameter of the eye is measured (see the above-described method).
c) Thereafter, a conversion of the measured wavefront to a desired pupil diameter takes place.
d) Thereafter, a determination of the caustic in the region of, for example, +/−3 dpt about the mean sphere mSph of the far point refraction $A_R$ takes place. Caustic is understood to be the enveloping of the rays in the image space for spherical aberration (see Helmut Goersch, Zeiss Handbuch für Augenoptik, Edition 2000, page 35).
e) Thereafter, a summation of the intensities of each location in the region of, for example, +/−3 dpt takes place about the mean sphere mSph of the caustic in a cylinder volume about the optical axis oA.
f) The determination of the depth of field T then takes place from the distance of the two points along the caustic whereat the intensity is less about a specific threshold, for example, 19%, than the maximum intensity.

The addition (Add, $Add_{preliminary}$) in accordance with the invention is (in general, initially) determined monocularly. The addition (Add, $Add_{preliminary}$) can be determined binocularly in that, for example, the same addition (Add, $Add_{preliminary}$) is used for the vision assist of both eyes. Here, for example, the mean value of the respective monocularly determined additions (Add, $Add_{preliminary}$) can be selected. Alternatively, for example, for the vision assist of both eyes, the larger of the additions (Add, $Add_{preliminary}$), which were determined for the two vision assists, can be used.

BRIEF DESCRIPTION OF THE DRAWINGS

The invention is explained in the following in greater detail with reference to the drawings.

FIG. 1 is a flowchart which indicates the individual method steps of an embodiment of a method of the invention for determining the individually required addition Add of a vision aid for a test person;

FIG. 2 shows an arrangement which is suitable for determining the individually required addition Add according to the method shown in FIG. 1;

Figure 15:
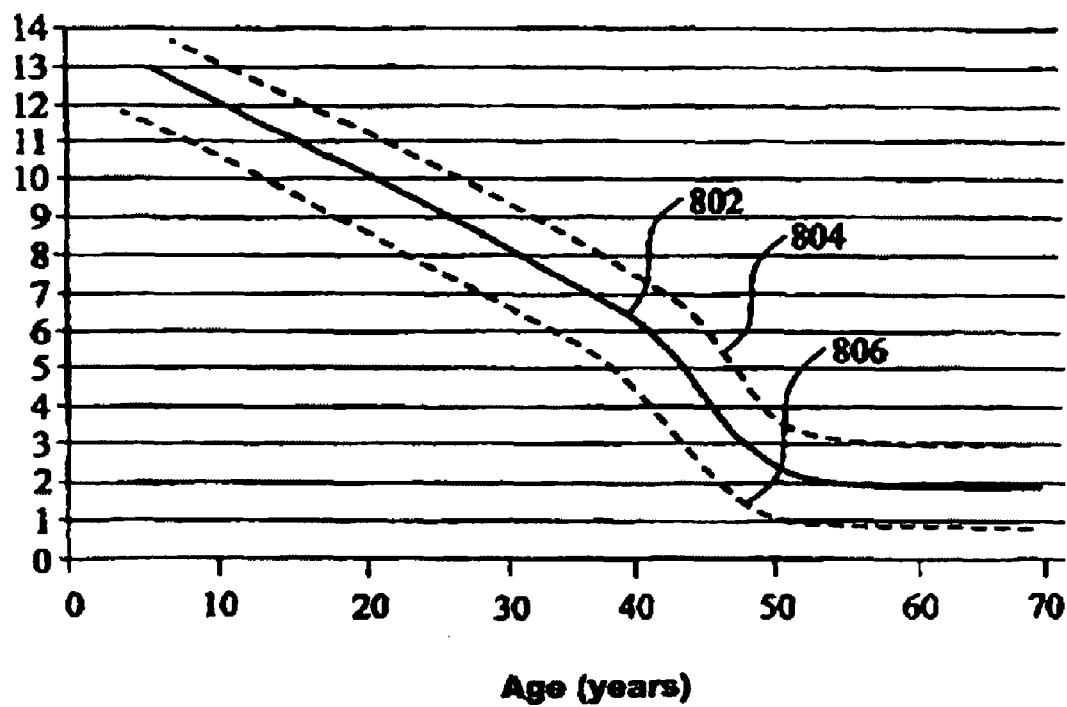
Figure 16:
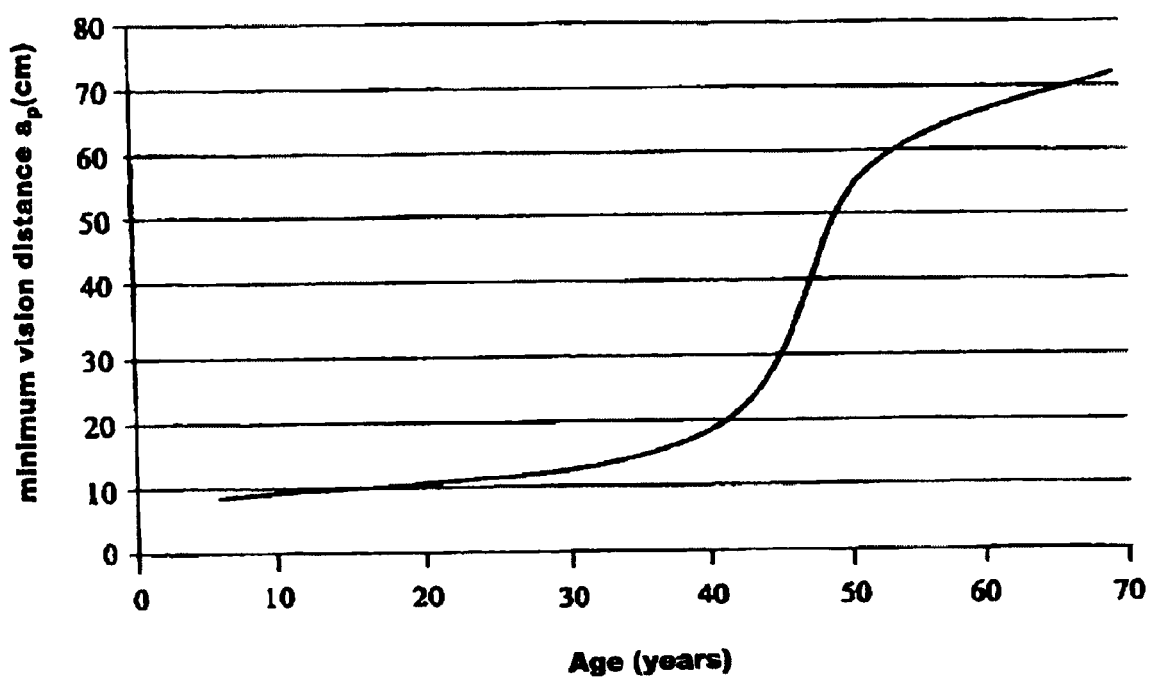
Figure 17:
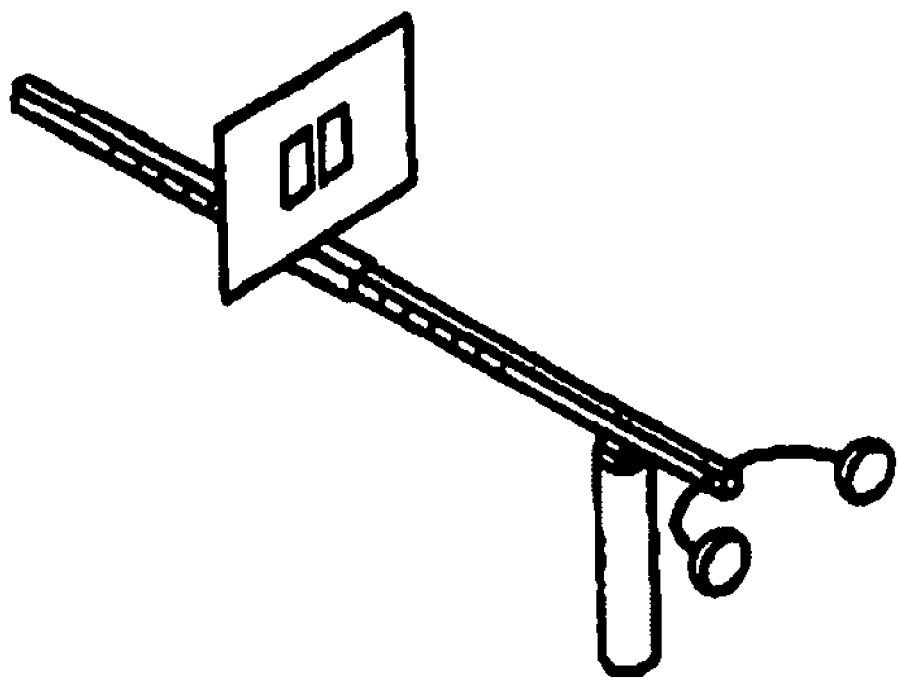

A: individual use accommodation $\Delta A_{use,50}$ of a 50 year old;

B: individual maximum amplitude of accommodation $\Delta A_{max,50}$ of a 50 year old;

C: mean maximum amplitude of accommodation $\Delta A^*_{max,m,50}$ of a 50 year old according to Duane;

D: mean maximum amplitude of accommodation $\Delta A^*_{max,m,30}$ of a 30 year old according to Duane;

E: ideal maximum amplitude of accommodation $\Delta A_{max}$;

FIG. 15 shows the age dependency of the mean physiological maximum amplitude of accommodation $\Delta A^*_{max}$ according to Duane (state of the art);

FIG. 16 shows the age dependency of the average vision distance (=near point distance) $a_p$ according to the state of the art; and, FIG. 17 shows an accommodation meter (state of the art).

DESCRIPTION OF THE PREFERRED
EMBODIMENTS OF THE INVENTION

Embodiment for the Determination of the Addition

FIG. 1 shows a flowchart from which the individual method steps of a variation of a method according to the invention can be taken for determining the individually required addition Add of a vision aid for the test person. FIG. 2 shows a corresponding arrangement for performing the method. Details as to the method as well as the arrangement are described hereinafter.

In a first step 100, a preliminary addition $Add_{preliminary}$ is determined for the vision aid (for example, a spectacle lens) of an eye of the test person. As a method for determining the preliminary addition $Add_{preliminary}$, one of the methods, which are known from the state of the art and which are described in the introductory description under methods 1 to 4 can be applied. For example, a method can be used wherein the test person selects the test spectacles which are most favorable to him from a plurality of test spectacles. It is also possible to use, as a preliminary addition $Add_{preliminary}$, the addition Add determined with the aid of the refraction unit 10 of FIG. 2. This refraction unit 10 can, for example, include a vision sample table or a transparent table illuminated from within. The lower edge of the vision sample must be disposed at least 1.40 m above the floor level. For example, a deflection mirror can be mounted on the opposite-lying wall and this deflection mirror can be so inclined that the test person recognizes the image of the vision sample in the center of the deflection mirror. The mirror center lies approximately at the eye elevation of the seated test person. Further details are set forth, for example, in Heinz Diepes, "Refraktionsbestimmung", Publisher Heinz Postenrieder, Pforzheim, 2nd Edition, 1975, page 28.

In a second step 200, the individual depth of field T of the eye of the test person is determined. The individual depth of field T of the eye of the test person can be objectively determined in the most different manner. A series of methods for the objective determination of the individual depth of field T is described hereinafter. Especially, a measuring unit 20 can also be used for the objective determination of the wavefront and the depth of field T as is shown in FIG. 2.

The actual addition Add then results in a third step 300 from the preliminary addition $Add_{preliminary}$ less the individual depth of field T weighted by a factor ω lying in the range between 0 and 1. As a weighting factor ω, for example, ½ or also ⅔ can be used. The computation can, for example, be performed with a conventional personal computer 30 as shown in FIG. 2. Addition determination, depth of field determination and addition computation can all take place also in a single computer which combines the components 10, 20 and 30 within itself.

The determination of the addition Add can be carried out separately monocularly or even binocularly sequentially for the vision aids (for example, spectacles) of both eyes. Vision aids with different additions ($Add_{left}$, $Add_{right}$) for the right and left eyes of the test person can be provided. It is, however, also possible that, for example, for the vision aids of both eyes of the test person, the same addition $Add=Add_{left}=Add_{right}$ can be used. As a common addition Add for both vision aids (for example, the lenses of spectacles), for example, the largest of the additions $Add=\max[Add_{left}, Add_{right}]$, which are determined for the respective vision aids of the eyes, can be used.

Further Embodiment for Determining the Addition

Figure 3:
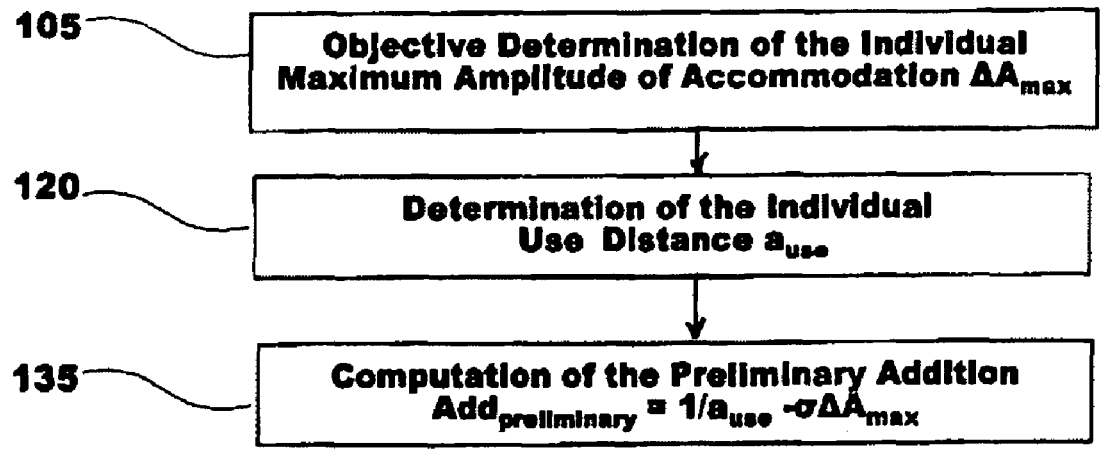
FIG. 3 is a flowchart which indicates the individual method steps of a further embodiment of a method of the invention for determining the individually required addition Add of a vision aid for a test person.

FIG. 3 shows a flowchart from which the individual method steps of a further variation of the method of the invention for determining the individually required addition Add of a vision aid for a test person can be seen.

In a first step 105, the individual maximum amplitude of accommodation $\Delta A_{max}$ is determined, deviating from the state of the art, not subjectively, that is, while considering the individual impression expressed by the test person, but is instead, objectively determined with one of the methods described hereinafter.

Figure 4:
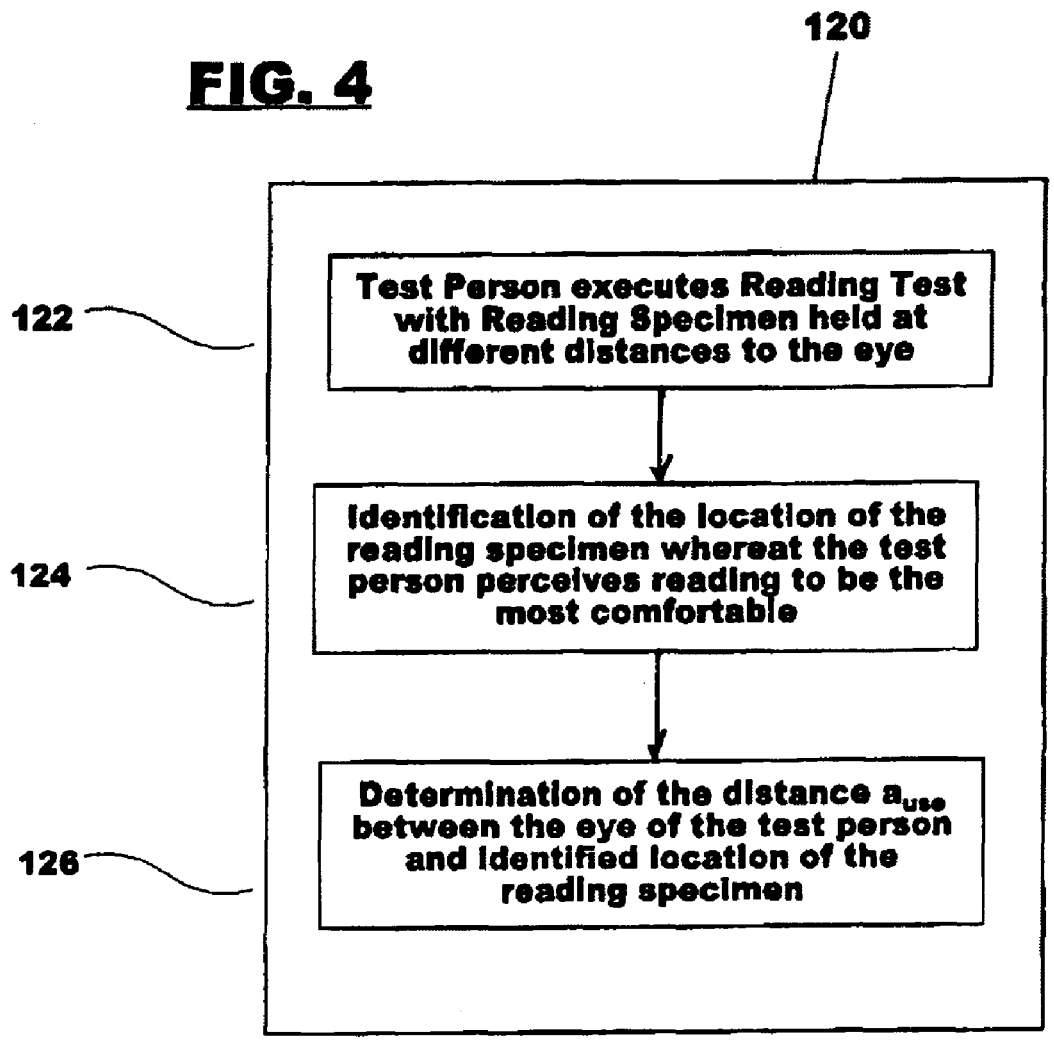
FIG. 4 is a, flowchart of an example for the determination of the individual use distance $a_{use}$ of a test person.

In a second step 120, the individual use distance $a_{use}$ of the test person is determined. The determination of the individual use distance $a_{use}$ of the test person can, for example, include the method steps shown in FIG. 4. In the example, the test person is handed a document as a reading sample. The test person is requested to hold the document at a distance comfortable for him and the test person is asked to read the content of the document (method step 122). The relative position of the document to the principal point $H_A$ of the eye is determined (method step 124). This can take place, for example, by evaluating an image of the reading test person in profile recorded by a camera. Thereafter, the distance $a_{use}$ is determined between the principal point $H_A$ of the eye of the test person and the location of the document (method step 126).

This distance $a_{use}$ defines the use distance $a_{use}$. It is also conceivable that a distance sensor is disposed on the reading sample (for example, as part of a display) which directly measures the distance $a_{use}$ to the principal point $H_A$ of the eye.

In step 135, the addition Add of the vision aid is computed (for example, with the aid of a suitable computation unit such as a computer) as the difference between the reciprocal of the use distance $a_{use}$, and the individual maximum amplitude of accommodation $\Delta A_{max}$ weighted by a factor σ. The weighting factor σ can assume values in a range greater than 0 and less than 1. According to the above-mentioned theory of Reiner, the weighting factor σ can have a value, for example, of ½. Schober suggests, for example, a value of ⅔.

Figure 5:
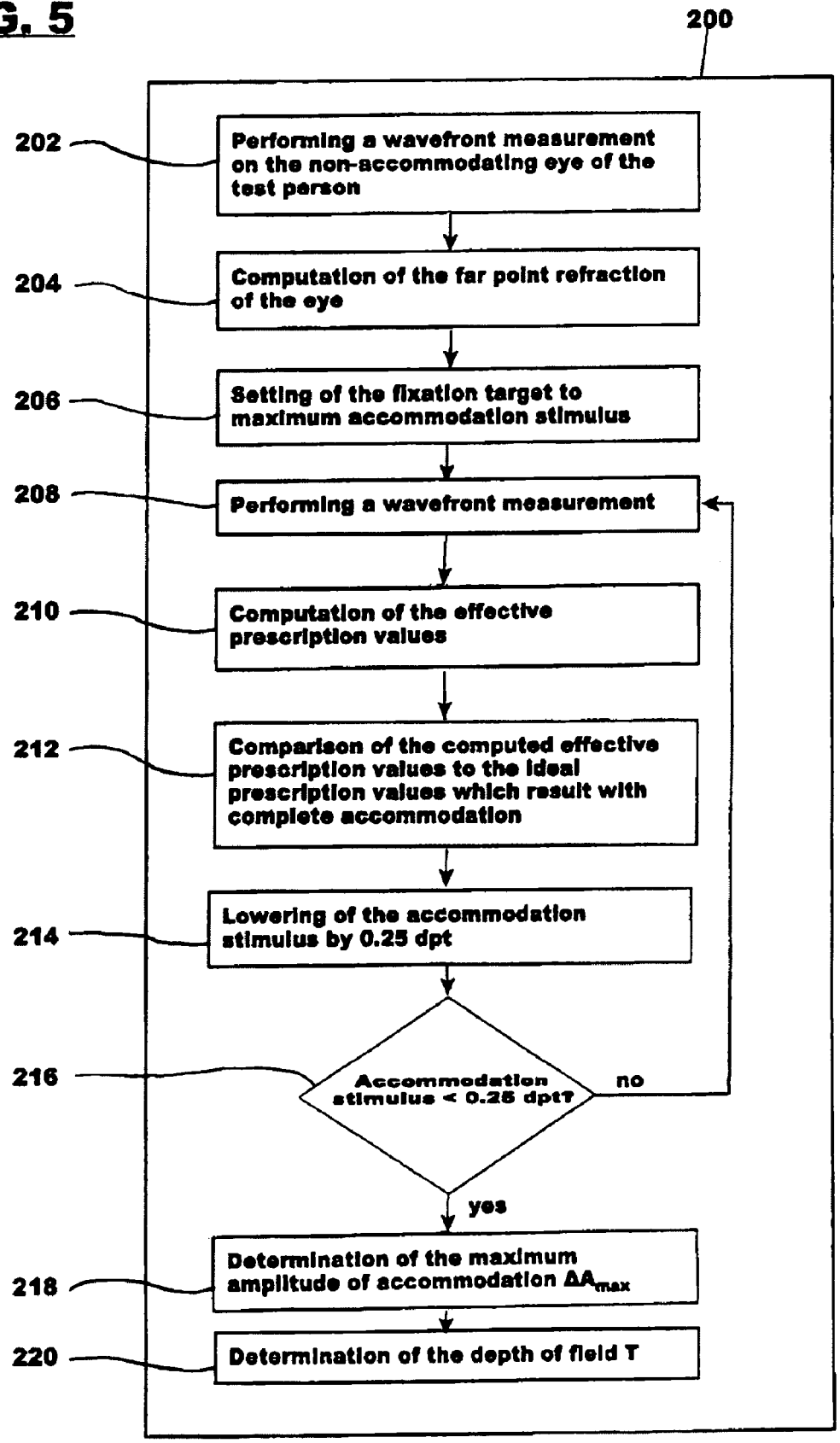
FIG. 5 is a flowchart of an example for the determination of the individual maximum amplitude of accommodation $\Delta A_{max}$ and the depth of field T of an eye of a test person.

Embodiment for Determining the Maximum Amplitude of Accommodation and the Depth of Field An example for a method 200 for determining the maximum amplitude of accommodation $\Delta A_{max}$ and the depth of field T, which is based on thoughts of the inventor, includes the method steps described in detail in the following and shown schematically in FIG. 5.

First a measurement 202 takes place of a wavefront, which is reflected at the retina, of a beam with a predetermined wavefront which impinges on the non-accommodating eye of the test person. Alternatively, an autorefractor measurement can be performed. From the measured wavefront or the autorefractor measurement, the far point refraction $A_R$ of the eye is then computed (method step 204).

Figure 6:
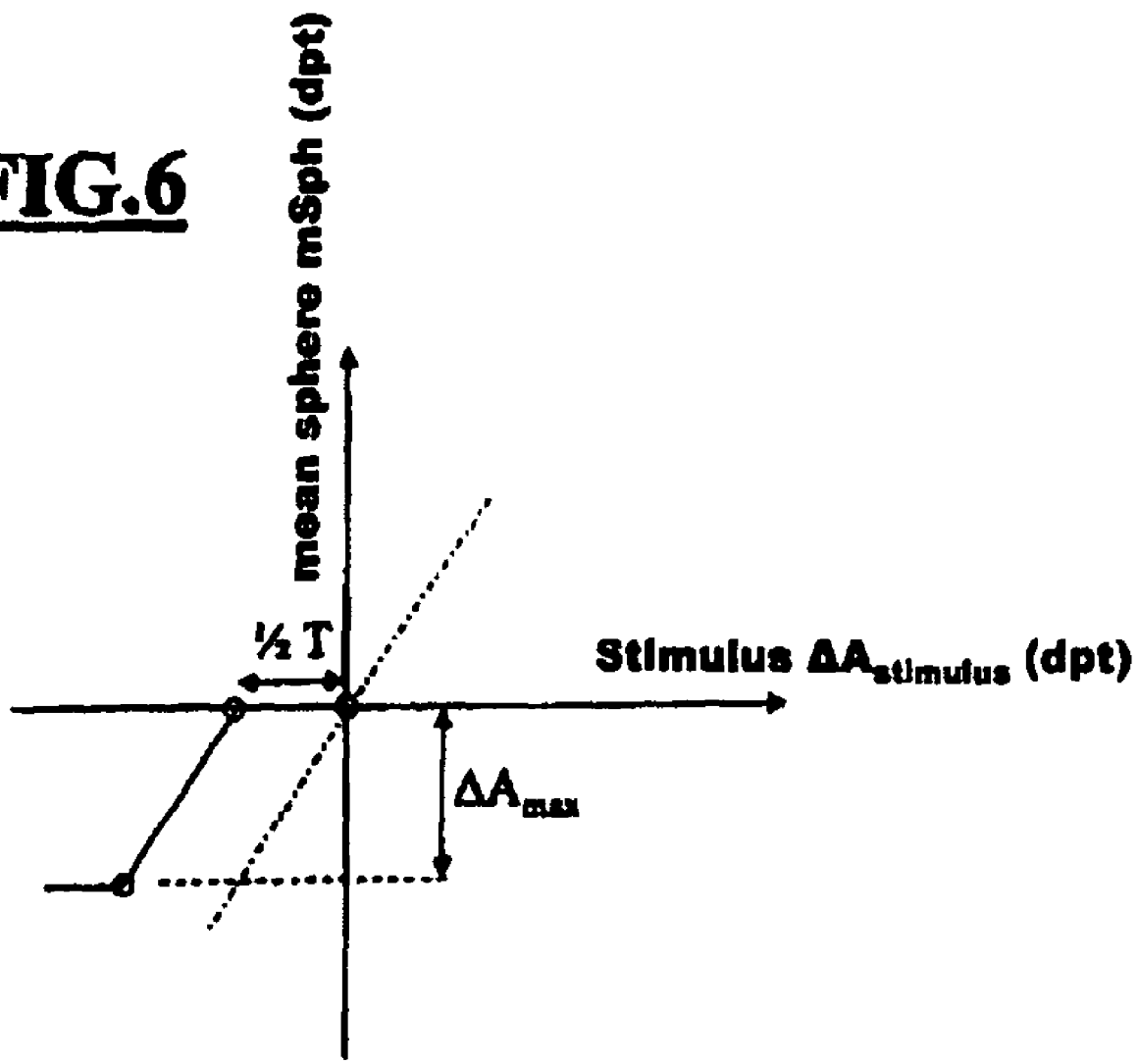
FIG. 6 shows the measured mean sphere mSph of the eye of a test person in dependence upon the accommodation stimulus $\Delta A_{stimulus}$.

Only then is the actual measurement of the maximum amplitude of accommodation $\Delta A_{max}$ carried out. For this purpose, the fixation target of the wavefront measurement unit or the autorefractor measurement unit is brought to the limit of the lower measuring range (step 206). This defines the accommodation stimulus $\Delta A_{stimulus}$, which is the maximum possible on the apparatus, for the eye of a test person. The ideal line between accommodation stimulus $\Delta A_{stimulus}$ in dpt and the amplitude of accommodation $\Delta A$ in dpt is fixed in the software. FIG. 6 shows the relationship between the mean sphere mSph (corresponding to equation (14)) of the eye of a test person and the accommodation stimulus $\Delta A_{stimulus}$, that is, the reciprocal of the distance of the fixation target from the principal point $H_A$ of the eye. The broken linearly running line defines the ideal case when the accommodation A which is reflected in a corresponding mean sphere mSph, always follows the accommodation stimulus $\Delta A_{stimulus}$.

Now a measurement of the wavefront or of the autorefractor values (method step 208) takes place and a computation takes place therefrom of the effective prescription values sphere, cylinder, axis of the eye (method step 210). The effective prescription values (sphere, cylinder, axis) are compared to the adjustment of the fixation target and stored (step 212). Now, the fixation target is changed in rapid steps with positive spherical effect Sph (step 212). Stated otherwise, this means that the fixation distance is reduced comparatively rapidly. Rapid here means that the eye cannot follow the change of the accommodation stimulus $A_{stimulus}$. For each change of the target in the direction of increasing positive spherical effect Sph plus, a new wavefront measurement or autorefraction measurement with subsequent computation of the far point refraction $A_R$ of the eye takes place. A change of the target with positive spherical effect Sph takes place up to far point refraction $A_R$ 3 dpt+3 dpt (step 216). The maximum amplitude of accommodation $\Delta A_{max}$ results then in the graphic of FIG. 6 from the vertical distance between the point on the measuring line whereat the test person for the last time did not accommodate and the point whereat the test person maximally accommodated for the first time (step 218). The depth of field T results from the twice horizontal difference between the point on the measuring line which lies on the far point refraction $A_R$ and the point whereat the test person did not accommodate the last time (step 220, FIG. 6).

Figure 7:
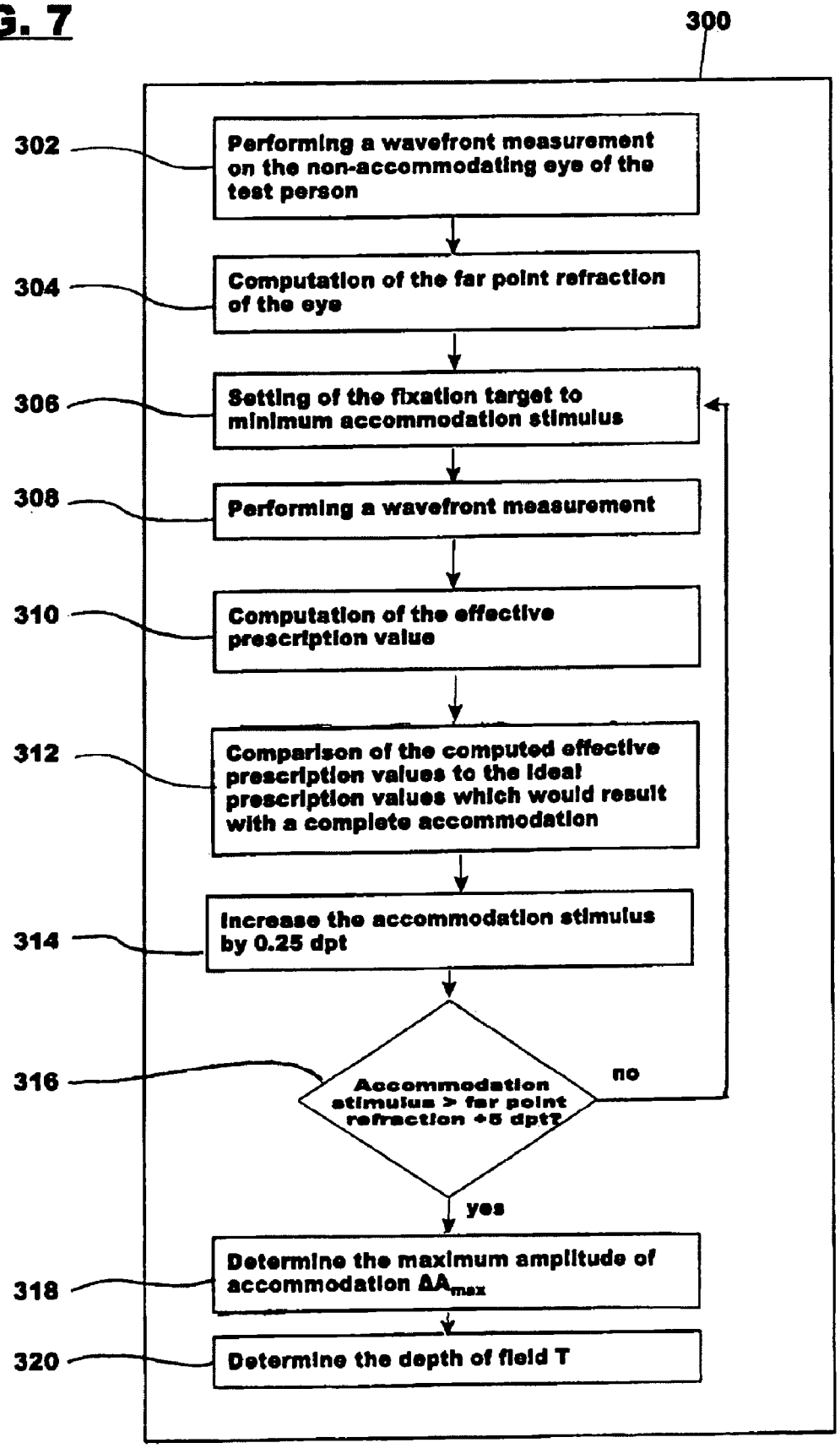
FIG. 7 shows a flowchart of a further embodiment for the determination of the individual maximum amplitude of accommodation $\Delta A_{max}$ and the depth of field T of the eye of a test person.

Additional Embodiment for Determining the Maximum Amplitude of Accommodation and the Depth of Field An additional example for a method 300 for determining the maximum amplitude of accommodation $\Delta A_{max}$ and the depth of field T includes the method steps shown schematically in FIG. 7 and described hereinafter.

First, as in the previous example, a measurement 302 takes place of the wavefront, which is reflected at the retina, of a beam having a predetermined wavefront which impinges on the non-accommodating eye of the test person. Alternatively, an autorefractor measurement can also be performed. The far point refraction $A_R$ of the eye is computed (method step 304) from the measured wavefront or the autorefractor measurement.

Thereafter, the target of the wavefront measurement unit or the autorefractor unit is brought to the limit of the upper measuring range (step 306).

A measurement of the wavefront (step 308) or of the autorefractor values takes place and therefrom a computation of the effective prescription values (spherical effect, cylindrical effect and axis position) Sph, Zyl, axis of the eye (step 310). These prescription values are compared to the adjustment of the target (step 312) and stored. Now, the target is changed in rapid steps in the direction of negative spherical effect Sph. For each change of the target in the direction minus, there is a new wavefront measurement or autorefractor measurement with subsequent computation of the far point refraction $A_R$ of the eye (step 316).

The maximum amplitude of accommodation $\Delta A_{max}$ results, in the graph of FIG. 6, from the vertical difference between the point on the measurement line whereat the test person was last maximally accommodated and the point whereat the test person for the first time did not accommodate (step 318). The depth of field T results from the twofold horizontal difference between the point on the measuring line, which lies on the far point refraction, and the point whereat the test person was not accommodated the last time (step 320, FIG. 6).

Embodiment for Determining the Depth of Field

Figure 8:
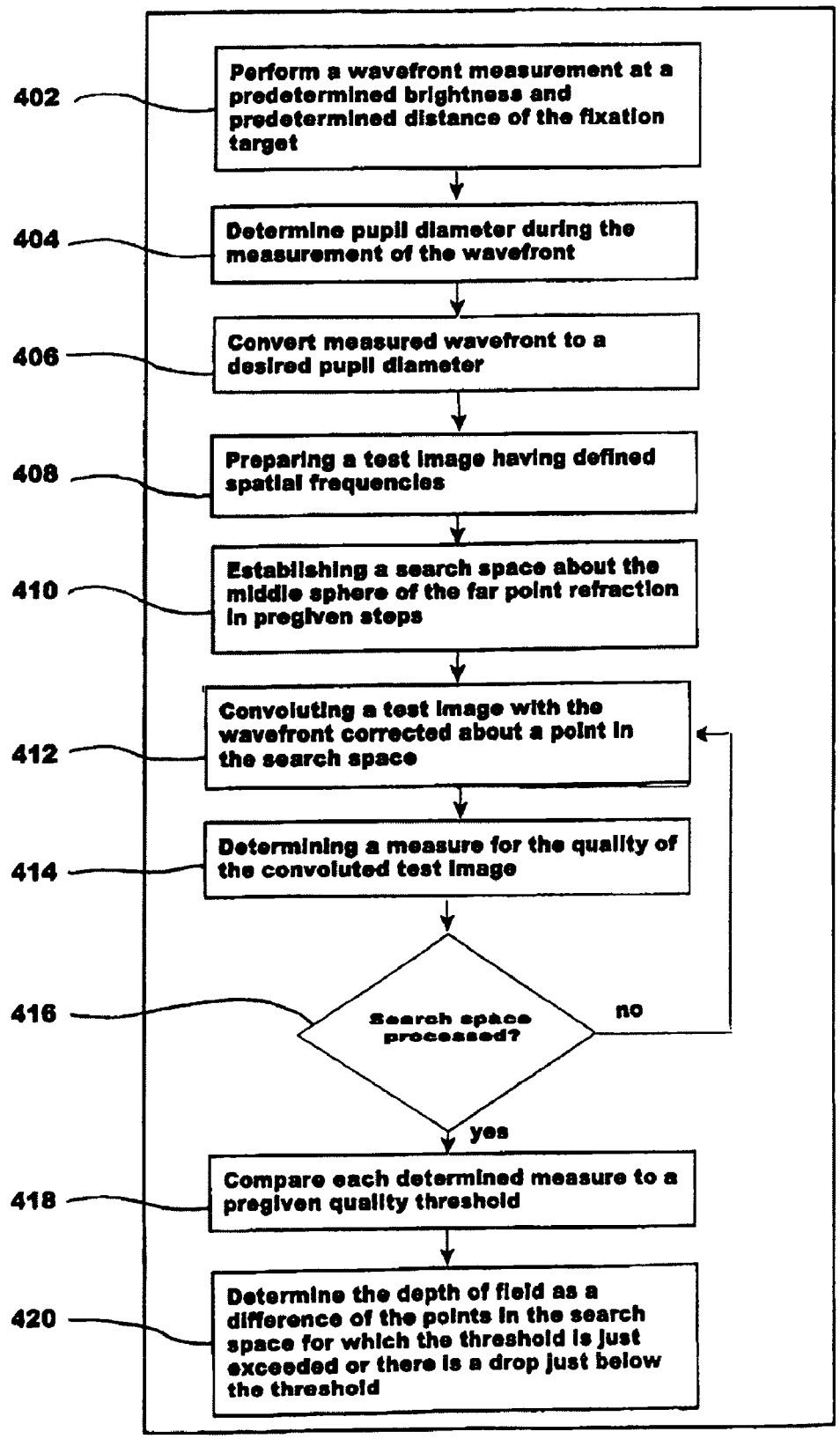
FIG. 8 shows a flowchart of an example for the determination of the individual depth of field T of the eye of a test person.

A method for determining the depth of field T on the basis of a wavefront analysis 400 can also include the method steps presented hereinafter and shown in FIG. 8.

In a first step, a wavefront measurement on one eye of the test person is performed (step 402) at predetermined brightness conditions and for a predetermined distance of a fixation target. The measurement conditions result from the individual problem pattern of the spectacles wearer, that is, from the anamnesis and can therefore here not be really determined.

The predetermined brightness determines the pupil size of the eye of the test person during the measurement. It is known that the pupil size, which adjusts because of the brightness conditions, can influence the measured wavefront considerably. The conditions for the measurement of the wavefront are, however, not perforce identical with the conditions under which the test person usually views an object, especially, the conditions in which a test person, for example, reads a newspaper. The invention therefore provides, in a further step 406, the conversion of the measured wavefront including the measured pupil diameter $P_{measurement}$ to a desired pupil diameter $P_{target}$. The desired pupil diameter $P_{target}$ can, for example, be the pupil diameter which would adjust if the test person would read the newspaper under daylight conditions. The desired pupil diameter $P_{target}$ can, for example, also be the diameter which would adjust if the test person would work at a computer screen under artificial illumination. It is apparent that the corresponding self-adjusting pupil diameters $P_{target}$ can be objectively determined, for example, by means of a video recording under most use conditions which are considered.

Figure 9:
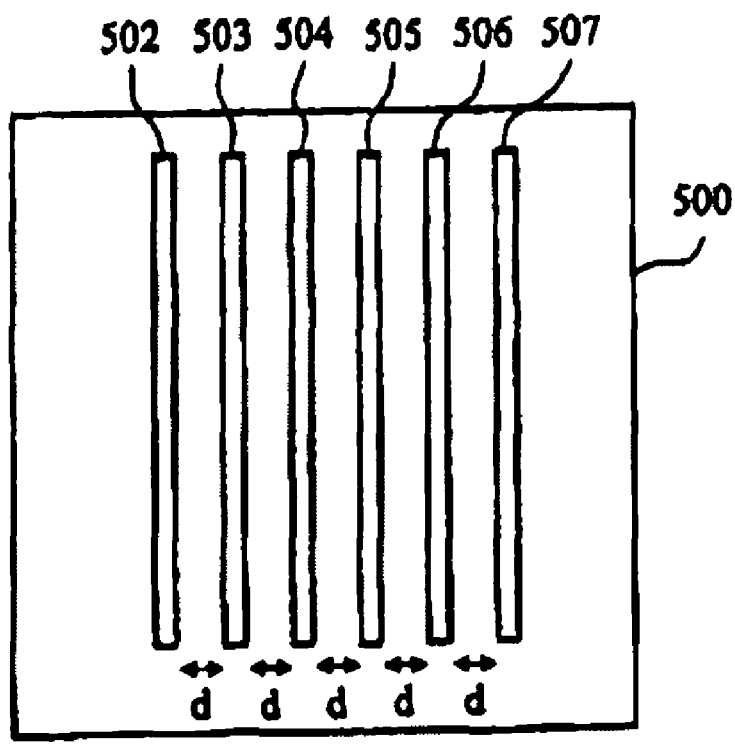
FIG. 9 shows an embodiment for a fixation target for performing the method of the flowchart of FIG. 8.

In a further method step, a fixation target is fixed having defined spatial frequencies corresponding to the desired requirements, for example, Visus V=0.4 when reading. An example of a pattern of this kind (test image 500) is shown in FIG. 9. In this example, the pattern comprises six strips (502, 503, 504, 505, 506, 507) which are arranged one next to the other at the same distance d. This fixation target 500 is, however, not presented to the test person as generally usual for viewing at a predetermined distance $a_{use}$; instead, the fixation target is determined by computation, for example, with the aid of a computer as the test person would perceive the pattern of the fixation target 500 if it would be made available to him at different distances $a_{use}$ to the principal point $H_A$ of the eye for viewing. Specifically, this takes place in the example in that first a search space $R_s$ of, for example, +/−3 dpt or +/−5 dpt is determined about the mean sphere mSph of the far point refraction $A_R$ in, for example, 0.05 dpt or 0.1 dpt steps (step 410). Thereafter, a convolution of the pattern of the target 500 takes place with the wavefront, which is corrected about the point in the search space (method step 412), that is, a determination of the perceptible pattern (502, 503, 504, 505, 506 and 507) of the fixation target 500 which perception is different based on the changed distance $a_{use}$ of the fixation target 500 to the principal point $H_A$ of the eye.

Figure 10:
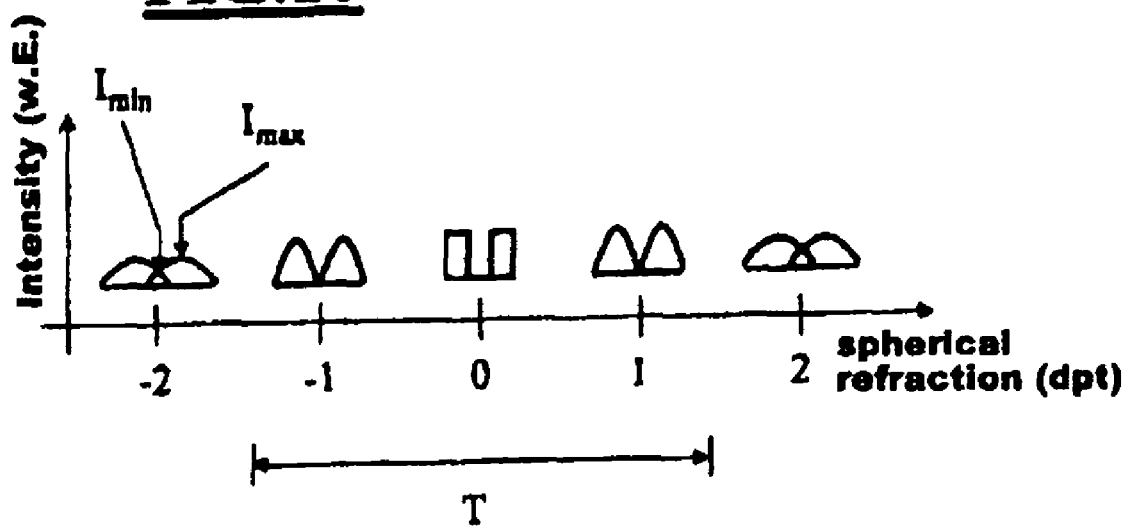
FIG. 10 is a schematic intensity profile as a measure for the perception of two mutually adjacent lines of the fixation target of FIG. 9 when the fixation target is disposed in the far point $A_R$ and at different distances to the far point.

In a next step 414, an evaluation takes place of the pattern (502, 503, 504, 505, 506 and 507) of the fixation target 500 with this pattern being obtained by the convolution. FIG. 10 shows the intensity profiles of two mutually adjacent lines (for example, 503 and 504 of FIG. 9) of the pattern (502, 503, 504, 505, 506 and 507) of the fixation target 500 after convolution in dependence upon the mean sphere mSph, that is, the sum of the measured spherical and half spherical refraction values (Sph+Zyl/2). A measure for the quality of the perceptibility of the pattern is the separate perceptibility of mutually adjacent lines with increased intensity I, the photometric contrast. From "Principles of Optics" referred to above, it is, for example, known that intensity differences ΔI of mutually adjacent lying regions are then separately perceivable when the lower intensity $I_{min}$ departs more than 19% from the stronger intensity $I_{min}$. The invention therefore provides determining, for example, the intensity maximum $I_{max}$ and the intensity minimum $I_{min}$ of the determined intensity profile I (as shown, for example, in FIG. 10) and to compute the difference ΔI of these determined extreme values ($I_{min}$, $I_{max}$) an to compare the value obtained therefrom to a pregiven threshold value S (for example, the value of 19%) and this for all values $mSph_{corr}$ within the search space (steps 416, 418). As depth of field T, the difference of the points in the search space is fixed for which the threshold S is just exceeded or there is a drop just therebelow.

Additional Embodiment for Determining the Depth of Field

Figure 11:
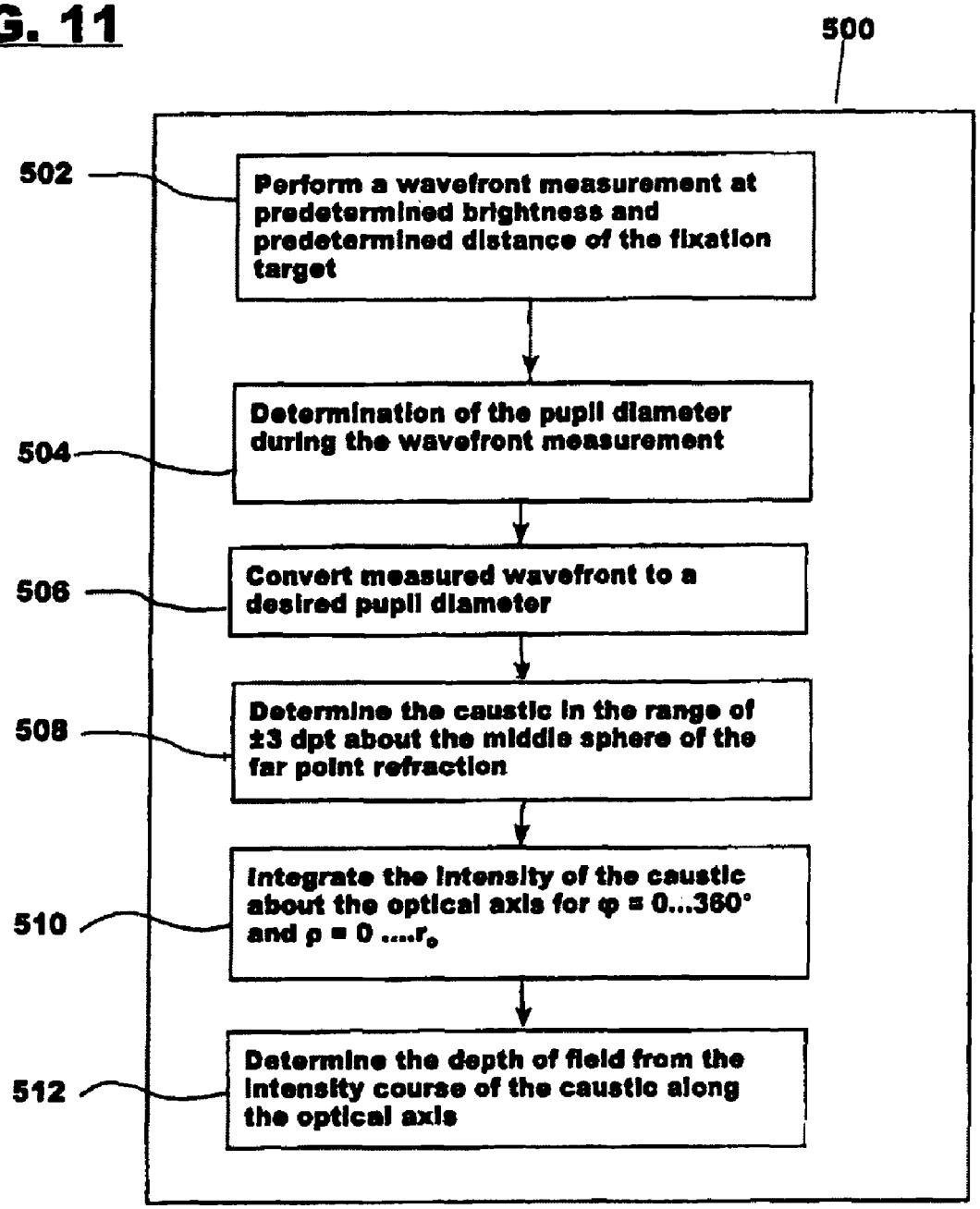
FIG. 11 is a flowchart of a second example for the determination of the individual depth of field T of the eye of the test person.
Figure 12:
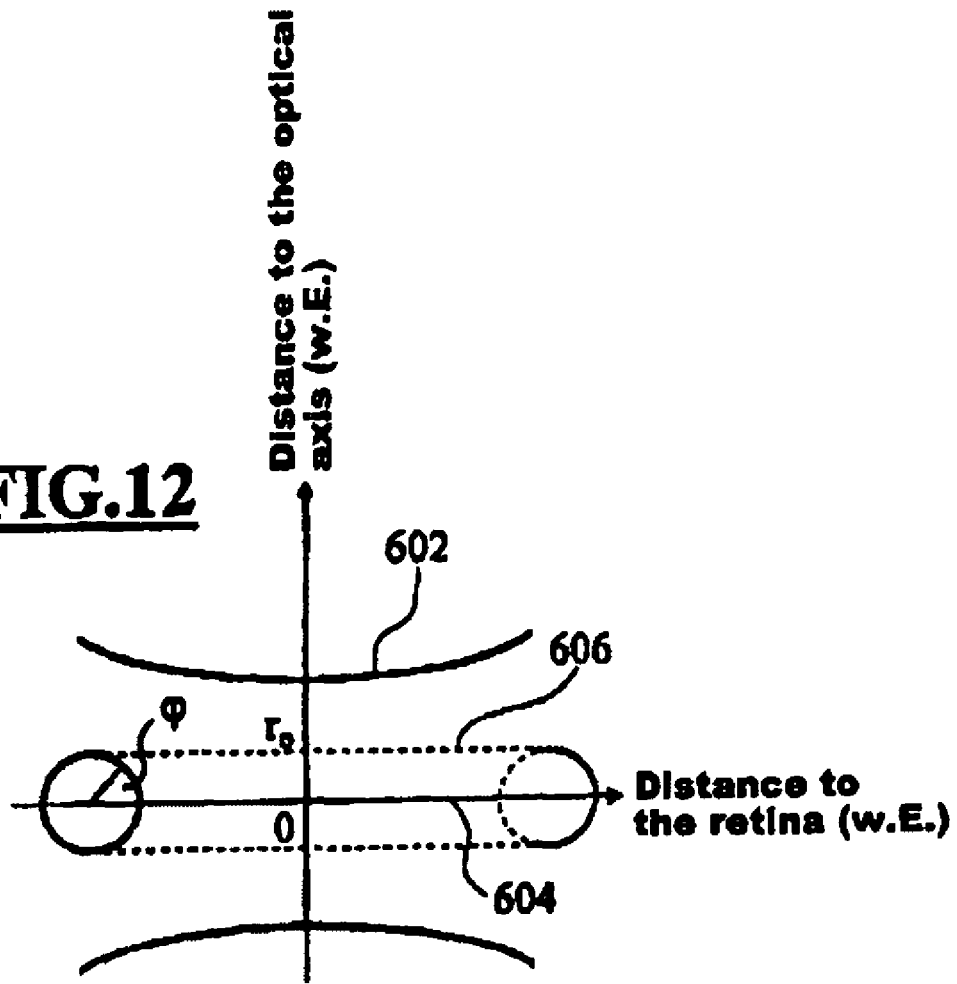
FIG. 12 is a longitudinal section through the caustic of a beam, which impinges upon the eye of a test person, with an input planar wavefront in the region of the retina.

A further method for determining the depth of field T on the basis of a wavefront analysis is explained in the following with reference to FIGS. 11 to 13.

The method again proceeds from a wavefront measurement 502 for predetermined brightness conditions and for a predetermined distance $a_{Fixation}$ of a fixation target. Thereafter, a conversion 504 of the measured wavefront to a desired pupil diameter $P_{target}$ (step 506) takes place in the manner described in the above embodiment.

In a further step 508, the caustic is computer determined in the range of, for example, ±3 dpt or ±5 dpt about the mean sphere of the far point refraction $A_R$. Caustic 602 is understood, as shown in FIG. 12, the more or less narrow constriction of a beam, which restriction arises in lieu of an image point and which beam shows, as a consequence of image errors, the beam emanating from an image point before it diverges again. Specifically, for example, the point scatter function PSF is determined by computation at a plurality of locations $a_{NH}$ about the retina of the non-accommodating eye of the test person with the eye being directed to the far point $A_R$.

Thereafter, an integration 510 of the intensity of the caustic 602 takes place up to a pregiven distance $r_0$ to the optical axis 604. This integration of the intensity of the caustic 602 is shown by the cylindrical volume 606 in FIG. 12 which is given by the integration angle φ=0 . . . 360° and the distance ρ=0 . . . $r_0$ to the optical axis 604. The distance $r_0$ can, for example, be set equal to the reciprocal of the required Visus V. FIG. 13 shows the intensity course of the caustic 602 along the optical axis 604. The intensity course is enclosed within the cylindrical volume 606.

Figure 13:
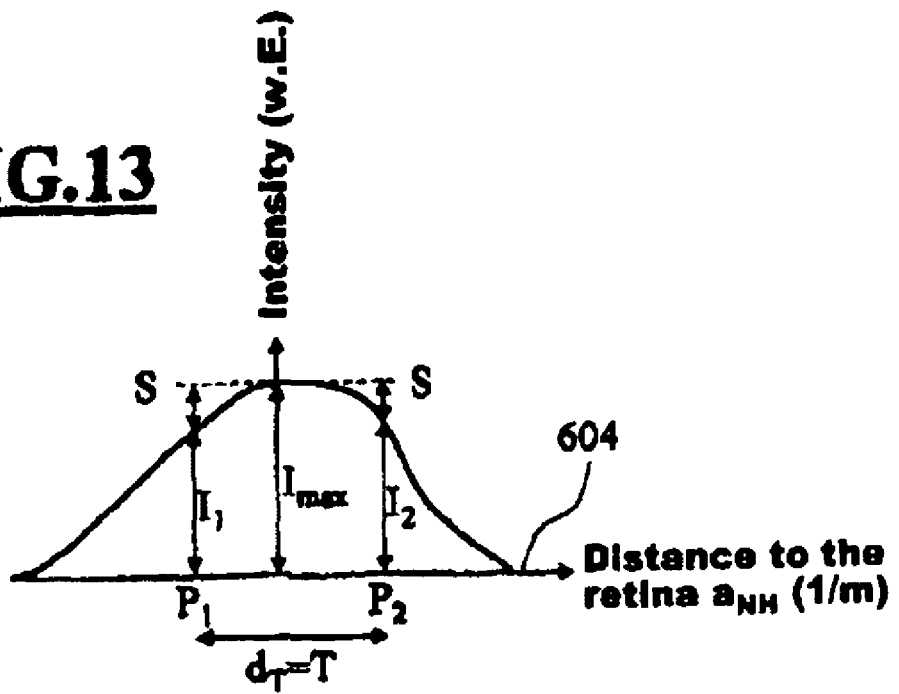
FIG. 13 shows the light intensity, which is enclosed in a cylinder in the region of the caustic of FIG. 12, in dependence upon the distance $a_{NH}$ from the retina plane.

According to the illustration of FIG. 13, the depth of field T is determined from the distance $d_T$ of the two points ($P_1$, $P_2$) along the optical axis 604 whereat the intensity $I_1$, $I_2$) is less than the maximum intensity by a specific threshold S, for example, 19% (step 512).

Embodiment for Determining the Depth of Field for Another Use Condition

It has been shown that the threshold S starting at which the different intensities $I_i$ can be perceived as such is very greatly dependent upon each test person. It is therefore purposeful to individually determine this threshold S and to determine therewith the depth of field T with still greater precision.

A method for the individual determination of the depth of field T on the basis of a wavefront analysis scaled to a desired or pregiven pupil diameter $P_{target}$ can include the following method steps.

From one of the methods first described above, one obtains, for example, the depth of field T1 for a first pupil diameter P1. According to one of the alternative above-mentioned methods, the individual threshold $s_{ind}$ is so determined with a second pupil diameter P2=P1 that the depth of field T2 computed therefrom is equal to the measured depth of field T1.

Thereafter, the depth of field T can be determined with one of the alternative above-mentioned methods for a pregiven pupil diameter $P_{target}$ (for example, 3.5 mm) and the threshold $S_{ind}$ determined in the previous step. If P1 is less than the desired pupil diameter $P_{target}$, then T2=T1.

SUMMARY

Figure 14:
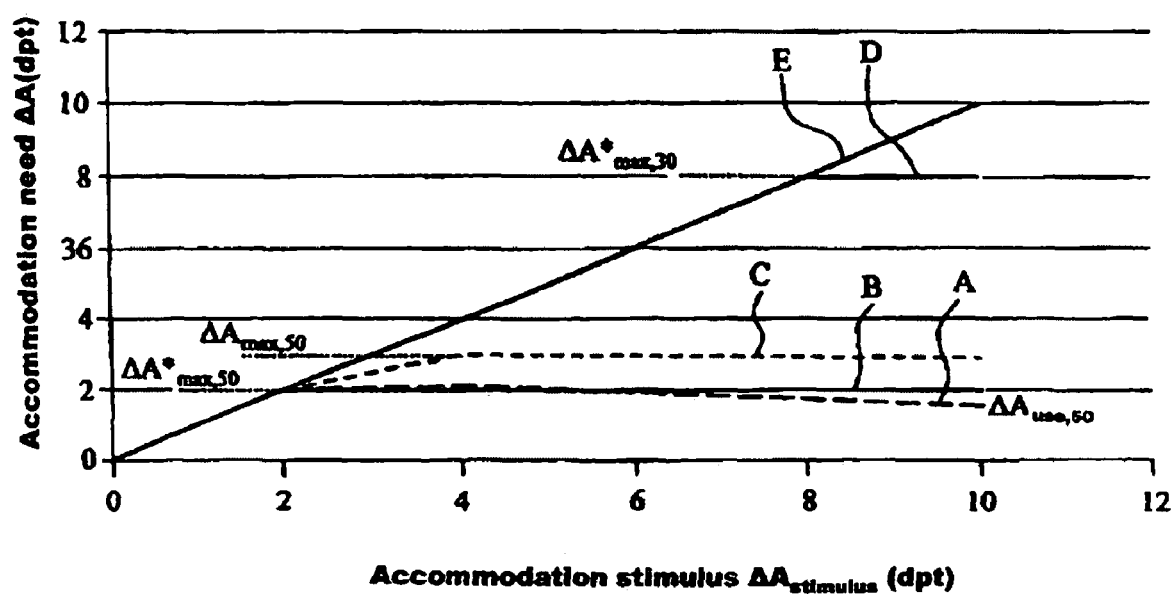
FIG. 14 is a diagram wherein the accommodation A of an eye of different test persons is plotted as a function of the accommodation stimulus $\Delta A_{stimulus}$.

FIG. 14 shows a diagram to make clear the differences with respect to the state of the art. In FIG. 14, the accommodation A of an eye of different test persons is plotted as a function of accommodation stimulus $\Delta A_{stimulus}$. Curve E defines the linear course of the ideal accommodation $A_{ideal}$. The ideal eye is in the position to compensate every accommodation stimulus $\Delta A_{max}$ via a corresponding accommodation $A_{ideal}$.

For comparison, the mean accommodation $A_{m,30}$ of a 30 year old is given by curve D and the mean accommodation $A_{m,50}$ of a 50 year old according to Duane is given by curve C. The eye of an average 30 year old is able to compensate an accommodation stimulus $\Delta A_{stimulus}$ up to 8 dpt. For higher accommodation stimuli $\Delta A_{stimulus}$, the elasticity of the lens is missing from his eye. The eye of an average 50 year old is only able to compensate an accommodation stimulus $\Delta A_{stimulus}$ up to 2 dpt because the elasticity of the lens of his eye has already declined to this degree. His residual accommodation $\Delta A_{max}$ is 2 dpt.

It is clear to the person of ordinary skill that the maximum amplitude of accommodation $\Delta A_{max}$ is very different individually and does not only depend upon age. The curve A defines the determined use accommodation $\Delta A_{use}$ of a 50 year old test person. The curve B is the corresponding individual accommodation $A_{50}$ of the 50 year old test person. It shows that the eye of the test person actually still has a maximum amplitude of accommodation $\Delta A_{max}$ of 3 dpt. What is used is a use accommodation $\Delta A_{use}$ of approximately 2 dpt.

The method of the invention and the arrangement of the invention consider the objectively determinable and, if needed, also objectively determined parameters maximum amplitude of accommodation $\Delta A_{max}$ and depth of field T. This means that the new method is not dependent upon the compliance of the test person. This is especially of advantage when the vision aids for elderly or sick persons are to be adapted. Furthermore, it is not necessary to go back to the usual 0.25 dpt quantization of the addition Add; instead, the addition Add can be individually adapted which is a further step for individually optimizing vision aids. The consideration of the individual depth of field T affords the advantage that the addition Add can be selected as small as absolutely necessary with the result that especially spectacle lenses can be manufactured with soft design without losing visual acuity in the near region.

It is understood that the foregoing description is that of the preferred embodiments of the invention and that various changes and modifications may be made thereto without departing from the spirit and scope of the invention as defined in the appended claims.

What is claimed is:

1. A method for determining the individually required addition (Add) of a vision assist for an eye, the method comprising the steps of:
 a) determining a preliminary addition ($\text{Add}_{preliminary}$);
 b) individually determining the depth of field (T); and,
 c) computing the addition (Add) according to the following equation:

$\text{Add} = \text{Add}_{preliminary} - \omega T$;

wherein $\omega$ defines a real number which lies in the range $0 < \omega \leq 1$.

2. The method of claim 1, comprising the further steps of:
 a) determining the maximum accommodation stimulus ($\Delta A_{stimulus,max}$) whereat the eye just still not accommodates; and,
 b) setting the depth of field (T) equal to the twofold of the maximum accommodation stimulus ($\Delta A_{stimulus,max}$).

3. The method of claim 2, wherein the maximum accommodation stimulus ($\Delta A_{stimulus,max}$) is determined with the aid of a wavefront measurement or an autorefraction measurement.

4. The method of claim 1, wherein the preliminary addition ($\text{Add}_{preliminary}$) is determined based on an estimate of the physiological maximum amplitude of accommodation ($\Delta A^*_{max}$) and/or an estimate of the actual maximum amplitude of accommodation ($\Delta A_{max}$) and/or an estimate of the use accommodation ($\Delta A_{use}$).

5. The method of claim 4, wherein a use distance ($a_{use}$) is determined and the preliminary addition ($\text{Add}_{preliminary}$) is computed according to the following equation:
 $\text{Add}_{preliminary} = 1/a_{use} - \sigma \Delta A^*_{max}$, wherein $\sigma$ defines a real number which lies in the range $0 \leq \sigma \leq 1$.

6. The method of claim 5, wherein the physiological maximum amplitude of accommodation ($\Delta A^*_{max}$) is measured individually by:
 i) measuring a near point distance ($a_p$) within a time (t) less than the accommodation time ($t_A$); and,
 ii) computing the physiological maximum amplitude of accommodation ($\Delta A^*_{max}$) according to the following equation:

$$\Delta A^*_{max} = \frac{1}{a_p}.$$

7. The method of claim 5, wherein the use distance ($a_{use}$) is determined individually as follows:
 i) an object is presented to a test person; and,
 ii) as use distance ($a_{use}$), the distance is taken from the object end principal point ($H_A$) of the eye to the location whereat the object is located during a relaxed viewing by the test person.

8. The method of claim 5, wherein the use distance ($a_{use}$) is determined by the test person via anamnesis with input of the principal vision tasks and the corresponding distances.

9. The method of claim 5, wherein the use distance ($a_{use}$) is determined objectively individually as follows in that a measurement unit automatically measures the distance ($a_{object}$) from an object to the object end principal point ($H_A$) of the eye.

10. The method of claim 5, wherein the actual maximum amplitude of accommodation ($\Delta A_{max}$) is determined from a wavefront measurement.

11. The method of claim 10, wherein the actual maximum amplitude of accommodation ($\Delta A_{max}$) is determined as follows:
 a) the far point refraction ($A_R$) and the near point refraction ($A_p$) are determined from a wavefront measurement or an autorefraction measurement of the eye; and,
 b) the actual maximum amplitude of accommodation ($\Delta A_{max}$) is computed as difference between far point refraction ($A_R$) and the near point refraction ($A_p$) as measured in step a).

12. The method of claim 4, wherein a use distance ($a_{use}$) is determined and the preliminary addition ($\text{Add}_{preliminary}$) is computed according to the equation:
 $\text{Add}_{preliminary} = 1/a_{use} - \sigma \Delta A_{max}$; wherein $\sigma$ defines a real number which lies in the range $0 \leq \sigma \leq 1$.

13. The method of claim 1, wherein the preliminary addition ($\text{Add}_{preliminary}$) is determined on the basis of an individual measurement of the physiological maximum amplitude of accommodation ($\Delta A^*_{max}$) and/or an individual measurement of the actual maximum amplitude of accommodation ($\Delta A_{max}$) and/or an individual measurement of the actual use accommodation ($\Delta A_{use}$).

14. The method of claim 4, wherein a use distance ($a_{use}$) is determined and the preliminary addition ($\text{Add}_{preliminary}$) is computed according to the following equation:

$\text{Add}_{preliminary} = 1/a_{use} \Delta A_{use}$.

15. The method of claim 14, wherein the actual use accommodation ($\Delta A_{use}$) is measured as follows:
 a) measuring the focusing point distance $a_E$ within a time (t) longer than the accommodation time ($t_A$); and,
 b) computing the use accommodation ($\Delta A_{use}$) according to the following equation:

$\Delta A_{use} = 1/a_E$.

16. The method of claim 1, wherein the preliminary addition ($Add_{preliminary}$) is computed according to the following equation:

$Add_{preliminary}=A_p$; wherein $A_p$ defines the near point refraction.

17. The method of claim 1, wherein the addition (Add) is determined monocularly or binocularly.

18. The method of claim 17, wherein the same addition (Add) is used for the vision assist of both eyes.

19. The method of claim 18, wherein, for the vision assist of both eyes, the larger of the additions ($Add_{left}$, $Add_{right}$) is used with the additions ($Add_{left}$, $Add_{right}$) being determined for the two vision assists.

20. A method for determining the individually required addition (Add) of a vision assist for an eye, the method comprising the steps of:
 a) determining the maximum amplitude of accommodation ($\Delta A_{max}$) individually and objectively;
 b) determining the use distance ($a_{use}$) individually; and,
 c) computing the addition (Add) in accordance with the following equation: $Add=1/a_{use}-\sigma\Delta A_{max}$; wherein $\sigma$ defines a real number which lies in the range $0<\sigma\leq 1$.

21. The method of claim 20, wherein the use distance ($a_{use}$) is determined individually as follows:
 i) an object is presented to a test person; and,
 ii) as use distance ($a_{use}$), the distance is taken from the object end principal point ($H_A$) of the eye to the location whereat the object is located during a relaxed viewing by the test person.

22. The method of claim 21, wherein the use distance ($a_{use}$) is determined by the test person via anamnesis with input of the principal vision tasks and the corresponding distances.

23. The method of claim 22, wherein the use distance ($a_{use}$) is determined objectively individually as follows in that a measurement unit automatically measures the distance ($a_{object}$) from an object to the object end principal point ($H_A$) of the eye.

24. The method of claim 23, wherein the actual maximum amplitude of accommodation ($\Delta A_{max}$) is determined from a wavefront measurement.

25. The method of claim 24, wherein the actual maximum amplitude of accommodation ($\Delta A_{max}$) is determined as follows:
 a) the far point refraction ($A_R$) and the near point refraction ($A_p$) are determined from a wavefront measurement or an autorefraction measurement of the eye; and,
 b) the actual maximum amplitude of accommodation ($\Delta A_{max}$) is computed as difference between far point refraction ($A_R$) and the near point refraction ($A_p$) as measured in step a).

26. The method of claim 20, wherein the addition (Add) is determined monocularly or binocularly.

27. The method of claim 26, wherein the same addition (Add) is used for the vision assist of both eyes.

28. The method of claim 27, wherein, for the vision assist of both eyes, the larger of the additions ($Add_{left}$, $Add_{right}$) is used with the additions ($Add_{left}$, $Add_{right}$) being determined for the two vision assists.

29. An arrangement for determining the individually required addition (Add) of a vision assist for an eye, the arrangement comprising:
 a) an addition determination unit for determining a preliminary addition ($Add_{preliminary}$);
 b) a depth of field determination unit in order to individually determine the depth of field (T) of the eye; and,
 c) an addition computation unit to compute the addition (Add) according to the following equation:

$Add=Add_{preliminary}-\omega T$; wherein $\omega$ defines a real number which lies in the range $0<\omega<1$.

30. The arrangement of claim 29, wherein:
 i) an accommodation stimulus determination unit is provided to determine the maximum accommodation stimulus ($\Delta A_{stimulus,max}$) whereat the eye is just not accommodated; and,
 ii) the depth of field determination unit sets the depth of field (T) equal to the twofold of the maximum accommodation stimulus ($\Delta A_{stimulus,max}$).

31. The arrangement of claim 30, wherein the accommodation stimulus determination unit includes a wavefront measuring unit or an autorefraction measuring unit.

32. The arrangement of claim 29, wherein the addition determination unit is adapted to determine an individual measurement of the physiological maximum amplitude of accommodation ($\Delta A^*_{max}$) and/or an individual measurement of the actual maximum amplitude of accommodation ($\Delta A_{max}$) and/or an individual measurement of the actual use accommodation ($\Delta A_{use}$).

33. The arrangement of claim 32, wherein a use distance determination unit is provided for determining the use distance ($a_{use}$) and the addition determination unit is adapted to compute the preliminary addition ($Add_{preliminary}$) according to the following equation: $Add_{preliminary}=1/a_{use}-\sigma\Delta A^*_{max}$; wherein $\sigma$ defines a real number which lies in the range $0\leq\sigma\leq 1$.

34. The arrangement of claim 32, wherein a use distance determination unit for determining the use distance ($a_{use}$) is provided and the addition determination unit is adapted to compute the preliminary addition ($Add_{preliminary}$) according to the following equation:

$Add_{preliminary}=1/a_{use}-\sigma\Delta A_{max}$; wherein $\sigma$ defines a real number which lies in the range $0\leq\sigma\leq 1$.

35. The arrangement of claim 34, wherein the maximum amplitude of accommodation determination unit includes a wavefront measuring unit.

36. An arrangement for determining the individual required addition (Add) of a visual assist for the eye, the arrangement comprising:
 a) an accommodation determination unit for individually and objectively determining the maximum amplitude of accommodation ($\Delta A_{max}$);
 b) a use distance determination unit for individually determining the use distance ($a_{use}$); and,
 c) an addition computation unit for computing the addition (Add) according to the following equation:

$Add=1/a_{use}-\sigma\Delta A_{max}$; wherein $\sigma$ defines a real number which lies in the range $0<\sigma<1$.

37. The arrangement of claim 36, wherein the maximum amplitude of accommodation determination unit includes a wavefront measuring unit.

38. A computer adapted to execute a method for determining the individually required addition (Add) of a vision assist for an eye, the method comprising the steps of:
 a) determining a preliminary addition ($Add_{preliminary}$);
 b) individually determining the depth of field (T); and,
 c) computing the addition (Add) according to the following equation:

$Add=Add_{preliminary}-\omega T$;

wherein $\omega$ defines a real number which lies in the range $0<\sigma\leq 1$.

39. A computer program stored on a non-transitory machine-readable data carrier, said computer program having a program code equipped for executing a method for determining the individually required addition (Add) of a vision assist for an eye when the method is run on a computer and comprises the steps of:
  a) determining a preliminary addition (Add$_{preliminary}$);
  b) individually determining the depth of field (T); and,
  c) computing the addition (Add) according to the following equation:

$$\text{Add} = \text{Add}_{preliminary} - \omega T;$$

wherein $\omega$ defines a real number which lies in the range $0 < \omega < 1$.

40. A computer program product stored on a non-transitory machine-readable data carrier, said computer program product having a program code equipped for executing a method for determining the individually required addition (Add) of a vision assist for an eye when the method is executed on a computer and comprises the steps of:
  a) determining a preliminary addition (Add$_{preliminary}$)
  b) individually determining the depth of field (T); and,
  c) computing the addition (Add) according to the following equation:

$$\text{Add} = \text{Add}_{preliminary} - \omega T;$$

wherein $\omega$ defines a real number which lies in the range $0 < \sigma \leq 1$.

41. A computer adapted to execute a method for determining the individually required addition (Add) of a vision assist for an eye, the method comprising the steps of:
  a) determining the maximum amplitude of accommodation ($\Delta A_{max}$) individually and objectively;
  b) determining the use distance ($a_{use}$) individually; and,
  c) computing the addition (Add) in accordance with the following equation: $\text{Add} = 1/a_{use} - \sigma \Delta A_{max}$; wherein $\sigma$ defines a real number which lies in the range $0 < \sigma \leq 1$.

42. A computer program stored on a non-transitory machine-readable data carrier, said computer program having a program code equipped for executing a method for determining the individually required addition (Add) of a vision assist for an eye when the method is run on a computer and comprises the steps of:
  a) determining the maximum amplitude of accommodation ($\Delta A_{max}$) individually and objectively;
  b) determining the use distance ($a_{use}$) individually; and,
  c) computing the addition (Add) in accordance with the following equation: $\text{Add} = 1/a_{use} - \sigma \Delta A_{max}$; wherein $\sigma$ defines a real number which lies in the range $0 < \sigma \leq 1$.

43. A computer program product stored on a non-transitory machine-readable data carrier, said computer program product having a program code equipped for executing a method for determining the individually required addition (Add) of a vision assist for an eye when the method is executed on a computer and comprises the steps of:
  a) determining the maximum amplitude of accommodation ($\Delta A_{max}$) individually and objectively;
  b) determining the use distance ($a_{use}$) individually; and,
  c) computing the addition (Add) in accordance with the following equation: $\text{Add} = 1/a_{use} - \sigma \Delta A_{max}$; wherein $\sigma$ defines a real number which lies in the range $0 < \sigma \leq 1$.

* * * * *

UNITED STATES PATENT AND TRADEMARK OFFICE
CERTIFICATE OF CORRECTION

PATENT NO. : 7,972,000 B2
APPLICATION NO. : 12/656143
DATED : July 5, 2011
INVENTOR(S) : B. Monique Becker, Jesús-Miguel Cabeza-Guillén and Timo Kratzer It is certified that error appears in the above-identified patent and that said Letters Patent is hereby corrected as shown below:

Page 2
Line 8: add -- JP -- before "Office".

In column 1:
Line 15: delete "a method" and substitute -- an arrangement -- therefor.

In column 6:
Line 16: delete "$\Delta A_{max}$" and substitute -- $\Delta A^*_{max}$ -- therefor.

In column 7:
Line 48: delete "Add=$1/a_{use-\sigma\Delta Amax}$" and substitute
-- Add=$1/a_{use}-\sigma\Delta A_{max}$ -- therefor.

In column 9:
Line 63: delete "$Add_{preliminary} = 1/a_{uge} - \sigma\Delta A_{max}$," and
substitute -- $Add_{preliminary} = 1/a_{use} - \sigma\Delta A_{max}$, -- therefor.

In column 10:
Line 20: add -- $a_{use}$ -- after "tances".
Line 21: delete "WO 2008/054379 A1" and substitute
-- WO 2008/064379 A1 -- therefor.
Line 23: delete "De" and substitute -- be -- therefor.

In column 11:
Line 55: delete "$Add_{preliminary}=1/a_{use} - \Delta A_{use}$." and substitute
-- $Add_{preliminary} = 1/a_{use} - \Delta A_{use}$. -- therefor.

In column 13 :
Line 57: delete "or" and substitute -- of -- therefor.

Signed and Sealed this
Eighth Day of November, 2011

David J. Kappos
*Director of the United States Patent and Trademark Office*

CERTIFICATE OF CORRECTION (continued)
U.S. Pat. No. 7,972,000 B2

In column 14:
Line 44: delete "a," and substitute -- a -- therefor.
Line 64: delete "$A_R$" and substitute -- $a_R$ -- therefor.

In column 16:
Line 62: delete "$a_{use}$," and substitute -- $a_{use}$ -- therefor.

In column 19:
Line 45: delete "an" and substitute -- and -- therefor.

In column 20:
Line 8: delete "$A_R$" and substitute -- $a_R$ -- therefor.
Line 22: delete "$(I_1,I_2)$" and substitute -- $(I_1, I_2)$ -- therefor.
Line 23: add -- $I_{max}$ -- after "intensity".

In column 24:
Line 2: delete "$0<\omega<1$." and substitute -- $0<\omega\leq1$. -- therefor.
Line 50: delete "$0<\sigma<1$." and substitute -- $0<\sigma\leq1$. -- therefor.

In column 25:
Line 11: delete "$0<\sigma<1$." and substitute -- $0<\sigma\leq1$. -- therefor.
Line 18: delete "($Add_{preliminary}$)" and substitute -- ($Add_{preliminary}$); -- therefor.